United States Patent
Khokhar et al.

(10) Patent No.: US 10,919,822 B2
(45) Date of Patent: Feb. 16, 2021

(54) DUAL CATALYST PROCESSES AND SYSTEMS FOR PROPYLENE PRODUCTION

(71) Applicant: Saudi Arabian Oil Company, Dhahran (SA)

(72) Inventors: Munir D. Khokhar, Khobar (SA); Faisal H. Alshafei, Khobar (SA); Noor A. Sulais, Dhahran (SA); Sohel K. Shaikh, Dhahran (SA); Raed H. Abudawoud, Khobar (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 16/390,523

(22) Filed: Apr. 22, 2019

(65) Prior Publication Data
US 2019/0241488 A1 Aug. 8, 2019

Related U.S. Application Data

(62) Division of application No. 15/866,772, filed on Jan. 10, 2018, now Pat. No. 10,329,225.
(Continued)

(51) Int. Cl.
*B01J 8/04* (2006.01)
*C07C 4/06* (2006.01)
(Continued)

(52) U.S. Cl.
CPC .............. *C07C 11/06* (2013.01); *B01J 8/02* (2013.01); *B01J 8/04* (2013.01); *B01J 8/0453* (2013.01);
(Continued)

(58) Field of Classification Search
None
See application file for complete search history.

(56) References Cited

U.S. PATENT DOCUMENTS

| 3,442,821 A | 5/1969 | Hilfman |
| 3,546,313 A | 12/1970 | Banks |

(Continued)

FOREIGN PATENT DOCUMENTS

| CN | 101531558 A | 9/2009 |
| CN | 102177223 A | 9/2011 |

(Continued)

OTHER PUBLICATIONS

Debecker et al. "Aerosol route to nanostructured WO3—SiO2—Al2O3 metathesis catalysts: Toward higher propene yield." Applied Catalysis A: General 470 (2014) 458-466. (Year: 2014).*
(Continued)

*Primary Examiner* — Jennifer A Leung
(74) *Attorney, Agent, or Firm* — Dinsmore & Shohl LLP

(57) ABSTRACT

Processes and multiple-stage catalyst systems are disclosed for producing propylene from butene by at least partially metathesizing butene in a metathesizing reaction zone having a metathesis catalyst to form a metathesis reaction product and at least partially cracking the metathesis reaction product in a cracking reaction zone having a cracking catalyst to form a cracking reaction product that includes propylene. The metathesis catalyst may be a mesoporous silica-alumina catalyst support impregnated with metal oxide having a mesoporous silica-alumina catalyst support comprising from 5 weight percent to 50 weight percent alumina. The cracking catalyst may be a MFI structured silica-containing catalyst. The cracking reaction zone may be downstream of the metathesis reaction zone.

20 Claims, 5 Drawing Sheets

Related U.S. Application Data

(60) Provisional application No. 62/448,495, filed on Jan. 20, 2017.

(51) Int. Cl.

| | |
|---|---|
| C07C 6/04 | (2006.01) |
| C07C 11/06 | (2006.01) |
| B01J 8/02 | (2006.01) |
| B01J 21/12 | (2006.01) |
| B01J 29/04 | (2006.01) |
| B01J 29/40 | (2006.01) |
| B01J 23/30 | (2006.01) |
| B01J 35/00 | (2006.01) |
| B01J 35/10 | (2006.01) |
| B01J 37/02 | (2006.01) |
| B01J 21/00 | (2006.01) |

(52) U.S. Cl.
CPC .............. *B01J 8/0457* (2013.01); *B01J 21/00* (2013.01); *B01J 21/12* (2013.01); *B01J 23/30* (2013.01); *B01J 29/045* (2013.01); *B01J 29/40* (2013.01); *B01J 35/002* (2013.01); *B01J 35/0006* (2013.01); *B01J 35/1042* (2013.01); *B01J 35/1061* (2013.01); *B01J 37/0201* (2013.01); *C07C 4/06* (2013.01); *C07C 6/04* (2013.01); *C07C 2521/12* (2013.01); *C07C 2523/28* (2013.01); *C07C 2523/30* (2013.01); *C07C 2523/36* (2013.01); *C07C 2529/40* (2013.01); *C07C 2529/78* (2013.01); *Y02P 20/52* (2015.11)

(56) References Cited

U.S. PATENT DOCUMENTS

| | | | |
|---|---|---|---|
| 3,586,731 A | 6/1971 | Heckelsberg | |
| 3,702,886 A | 11/1972 | Argauer et al. | |
| 3,728,415 A | 4/1973 | Arganbright | |
| 4,024,201 A | 5/1977 | Takahashi | |
| 4,071,471 A | 1/1978 | Banks et al. | |
| 4,575,575 A | 3/1986 | Drake et al. | |
| 4,609,769 A | 9/1986 | Kukes et al. | |
| 5,026,935 A | 6/1991 | Leyshon et al. | |
| 5,026,936 A | 6/1991 | Leyshon et al. | |
| 5,191,131 A | 3/1993 | Takahata et al. | |
| 5,439,859 A | 8/1995 | Durante et al. | |
| 5,523,502 A | 6/1996 | Rubin | |
| 5,877,365 A | 3/1999 | Chodorge et al. | |
| 6,159,433 A | 12/2000 | Chodorge et al. | |
| 6,207,115 B1 | 3/2001 | Chodorge et al. | |
| 6,210,562 B1 | 4/2001 | Xie et al. | |
| 6,538,168 B1 | 3/2003 | Schwab et al. | |
| 6,586,649 B1 | 7/2003 | Botha et al. | |
| 6,646,172 B1 | 11/2003 | Schwab et al. | |
| 6,777,582 B2 | 8/2004 | Gartside et al. | |
| 6,977,321 B1 | 12/2005 | Dath et al. | |
| 7,214,841 B2 | 5/2007 | Gartside et al. | |
| 7,754,647 B2 | 7/2010 | Schubert et al. | |
| 7,754,934 B2 | 7/2010 | Tsunoda et al. | |
| 7,977,522 B2 | 7/2011 | Takai et al. | |
| 8,299,313 B2 | 10/2012 | Takai et al. | |
| 8,324,440 B2 | 12/2012 | Popp et al. | |
| 8,362,308 B2 | 1/2013 | Stephan et al. | |
| 8,440,874 B2 | 5/2013 | Ramachandran et al. | |
| 8,586,813 B2 | 11/2013 | Ramachandran et al. | |
| 8,722,568 B2 | 5/2014 | Popp et al. | |
| 9,834,497 B2 | 12/2017 | Shaikh et al. | |
| 9,884,794 B2 | 2/2018 | Al-Khattaf et al. | |
| 2003/0176754 A1 | 9/2003 | Gartside et al. | |
| 2004/0254411 A1 | 12/2004 | Steinbrenner et al. | |
| 2005/0014981 A1 | 1/2005 | Gartside et al. | |
| 2005/0124839 A1 | 6/2005 | Gartside et al. | |
| 2006/0293548 A1 | 12/2006 | Spamer et al. | |
| 2007/0038010 A1 | 2/2007 | Xie et al. | |
| 2007/0225478 A1 | 9/2007 | Querci et al. | |
| 2008/0171655 A1 | 7/2008 | Creyghton et al. | |
| 2010/0041930 A1 | 2/2010 | Gartside et al. | |
| 2010/0168487 A1 | 7/2010 | Sawyer et al. | |
| 2010/0234542 A1 | 9/2010 | Blackborow et al. | |
| 2011/0021858 A1 | 1/2011 | Ramachandran et al. | |
| 2011/0152595 A1 | 6/2011 | Takai et al. | |
| 2011/0196185 A1 | 8/2011 | Krawczyk et al. | |
| 2012/0108864 A1 | 5/2012 | Gartside et al. | |
| 2012/0264990 A1 | 10/2012 | Nicholas et al. | |
| 2012/0283090 A1 | 11/2012 | Popp et al. | |
| 2012/0289617 A1 | 11/2012 | Wang et al. | |
| 2013/0085311 A1 | 4/2013 | Youn et al. | |
| 2013/0165701 A1 | 6/2013 | Zhou et al. | |
| 2013/0245348 A1 | 9/2013 | Vermeiren et al. | |
| 2014/0148629 A1 | 5/2014 | van Hal et al. | |
| 2015/0141720 A1 | 5/2015 | Ramachandran et al. | |
| 2015/0141721 A1 | 5/2015 | Choi et al. | |
| 2016/0130197 A1* | 5/2016 | Al-Khattaf | C07C 4/06 585/651 |
| 2016/0237006 A1 | 8/2016 | Stoyanova et al. | |
| 2017/0001925 A1 | 1/2017 | Abudawoud et al. | |
| 2017/0001926 A1 | 1/2017 | Shaikh et al. | |
| 2017/0001927 A1 | 1/2017 | Al-Khattaf et al. | |
| 2018/0057425 A1 | 3/2018 | Shaikh et al. | |
| 2018/0142167 A1 | 5/2018 | Al-Ghamdi et al. | |
| 2018/0208526 A1 | 7/2018 | Alshafei et al. | |
| 2018/0230071 A1 | 8/2018 | Bonduelle et al. | |

FOREIGN PATENT DOCUMENTS

| | | |
|---|---|---|
| CN | 102325742 A | 1/2012 |
| CN | 101531558 B | 4/2013 |
| CN | 102325742 B | 7/2014 |
| CN | 104370676 A | 2/2015 |
| DE | 10013253 A1 | 9/2001 |
| EP | 304515 B1 | 12/1991 |
| EP | 0920911 A1 | 6/1999 |
| EP | 2151424 A1 | 2/2010 |
| GB | 1205677 A | 9/1970 |
| JP | 2003500190 A | 1/2003 |
| JP | 2012500304 A | 1/2012 |
| KR | 20110056510 A | 5/2011 |
| KR | 20130059594 A | 6/2013 |
| NL | 8403050 A | 5/1986 |
| RU | 2370314 C1 | 10/2009 |
| WO | 9929805 A1 | 6/1999 |
| WO | 00/71255 A1 | 11/2000 |
| WO | 2006089957 A1 | 8/2006 |
| WO | 2009015118 A2 | 1/2009 |
| WO | 2009117128 A1 | 9/2009 |
| WO | 2010019595 A2 | 2/2010 |
| WO | 2008136280 A1 | 7/2010 |
| WO | 2011136983 A1 | 11/2011 |
| WO | 2015055594 A1 | 4/2015 |
| WO | 2017003812 A1 | 1/2017 |
| WO | 2017003817 A1 | 1/2017 |
| WO | 2017003821 A1 | 1/2017 |
| WO | 2018088815 A1 | 5/2018 |

OTHER PUBLICATIONS

Bortnovsky et al. "Cracking of pentenes to $C_2$—$C_4$ light olefins over zeolites and zeotypes. Role of topology and acid site strength and concentration." Applied Catalysis A: General 287 (2005) 203-213. (Year: 2005).*
Examination Report for Application No. GC 2018/34631 dated Aug. 22, 2019.
Notice of Allowance and Fee(s) due dated Oct. 18, 2019 pertaining to U.S. Appl. No. 16/039,983, filed Jul. 19, 2018, 29 pgs.
Machine translation claims of CN 102177223 A, Sep. 2011.
Machine translation description CN 102177223 A, Sep. 2011.
Arudra et al., "Silicalite-1 as Efficient Catalyst for Production of Propene from 1-Butene", ACS Catalysis, 2014, 4205-4212, 4, American Chemical Society.

(56) References Cited

OTHER PUBLICATIONS

Awayssa et al., "Modified HZSM-5 as FCC Additive for Enhancing Light Olefins Yield from Catalytic Cracking of VGO", Applied Catalysis A: General, 2014, 172-183, 477.
Balcar, et al., "Mesoporous molecular sieves as advanced supports for olefin metathesis catalysts", Coordination Chemistry Reviews 257, 2013, pp. 3107-3124, Czech Republic.
Barrett et al., "The Determination of Pore Volume and Area Distributions in Porous Substances. I. Computations from Nitrogen Isotherms", J. Am. Chem. Soc., 1951, 373-380, 73(1).
Beck et al., "A New Family of Mesoporous Molecular Sieves Prepared with Liquid Crystal Templates", J. Am. Chem. Soc., 1992, 10834-10843, 114, American Chemical Society.
Bhuiyan et al., "Kinetics Modelling of 2-Butene Metathesis Over Tungsten Oxide Containing Mesoporous Silica Catalyst", The Canadian Journal of Chemical Engineering, 2014, 1271-1282. 92.
Bhuiyan et al., "Metathesis of 2-Butene to Propylene over W-Mesoporous Molecular Sieves: A Comparative Study Between Tungsten Containing MCM-41 and SBA-15", Applied Catalysis A: General, 2013, 224-234, 467, Elsevier B.V.
Bin Hu, et al., "Highly Active Doped Mesoporous KIT-6 Catalysts for Metathesis of 1-Butene and Ethene to Propene: The Influence of Neighboring Environment of W Species", The Journal of Physical Chemistry, ACS Publication, 2013 American Chemical Society, pp. 26385-26395, USA.
Daniell et al., "Enhanced Surface Acidity in Mixed Alumina-Silicas: A Low-Temperature" FTIR Study:, 2000, 196, 247-260, Elsevier.
Do et al., "Zeolite Nanoclusters Coated onto the Mesopore Walls of SBA-15", J. Am. Chem. Soc., 2004, 14324-14325, 126, American Chemical Society.
International Search Report and Written Opinion dated Nov. 11, 2016 pertaining to International Application No. PCT/US2016/039025.
International Search Report and Written Opinion dated Sep. 14, 2016 pertaining to International Application No. PCT/US2016/039012.
International Search Report and Written Opinion dated Sep. 27, 2016 pertaining to International Application No. PCT/US2016/0038967.
International Search Report and Written Opinion dated Sep. 14, 2016 pertaining to International Application No. PCT/US2016/039013.
Jermy et al., "Utilization of ZSM-5/MCM-41 Composite as FCC Catalyst Additive for Enhancing Propylene Yield from VGO Cracking", J. Porous Mater, 2012, 499-509, 19, Springer.
Kawai et al., "Metaethesis of Halogen-Containing Olefin Over Re2O7/Al2O3 Catalyst Promited with Alkylmetal as a Cocatalyst", Journal of Molecular Catalysis A: Chemical, 1998, 133, 51-59.
Kumar et al., "Performance of Nano Crystalline H-ZSM-5 as Additive in FCC Catalyst: A Review", International Journal of Research in Engineering and Tehnology, May 2014, vol. 3, pp. 481-485.
Lwin et al., "Olefin Metathesis by Supported Metal Oxide Catalysts", ACS Catalysis, 2014, 2505-2520, 4, American Chemical Society.
Office Action pertaining to U.S. Appl. No. 15/190,950 dated Sep. 27, 2017.
Office Action pertaining to U.S. Appl. No. 15/190,964 dated Nov. 2, 2017.
Quignard et al., "Aryloxide Ligands in Metathesis of Olefins and Olefinic Esters: Catalytic Behaviour ofW(OAr)2Cl4 by SnMe4, Sn(n-Bu)4, Pb(n-Bu)4, MgNp2: synthesis of W(OAr)2Cl2(CHCMe3)(OR2) and W(OAr)2Cl(CHCMe3)(CH2CMe3)(OR2)", Journal of Molecular Catalysis, 1986, 36, 13-29.
Ruihua Gao, et al., "High-activity, single-site mesoporous WO3-MCF materials for the catalytic epoxidation of cycloocta-1,5-diene with aqueous hydrogen peroxide", Journal of Catalysis, 256, 2008, pp. 259-267, China.
Wang et al., "Synthesis and Structure of Silicalite-1/SBA-15 Composites Prepared by Carbon Templating and Crystallization", Journal of Materials Chemistry, 2007,4265-4273,17, The Royal Society of Chemistry 2007.
Wang et al., "Effect of Support Nature on WO3/SiO2 Structure and Butene-1 Metathesis", Applied Catalysis A: General, 2003, 25-37, 250, Elsevier B.V.
Zhao et al., "Effect of Tungsten Oxide Loading on Metathesis Activity of Ethene and 2-Butene Over WO3/SiO2 Catalysts" Transition Met Chem, 2009, 621-27, 34, Springer.
International Preliminary Report on Patentability dated Jan. 11, 2018—PCT/US2016/039012.
International Preliminary Report on Patentability dated Jan. 2, 2018—PCT/US2016/039012.
Non-Final Office Action pertaing to U.S. Appl. No. 15/398,196 dated Jan. 9, 2018.
Puriwat, et al., "Elucidation of the basicity dependence of 1-butene isomerization on MgO/Mg(OH)s catalysts", Catalysis Communications, 2010, pp. 80-85.
International Search Report and Written opinion dated Mar. 28, 2018, pertaining to International Application No. PCT/US2018/013945, filed Jan. 17, 2018, 9 pages.
U.S. Office Action dated Apr. 20, 2018 pertaining to U.S. Appl. No. 15/859,794, filed Jan. 2, 2018.
International Search Report and Written Opinion dated Apr. 24, 2018 pertaining to International Application No. PCT/US2018/014131, filed Jan. 18, 2018.
Notice of Allowance dated Apr. 24, 2018 pertaining to U.S. Appl. No. 15/190,964, filed Jun. 23, 2016.
Election/Restriction Requirement dated May 21, 2018, pertaining to U.S. Appl. No. 15/866,772, filed Jan. 10, 2018.
Korean Office Action pertaining to Korea Application No. 10-2018-7003238 dated May 14, 2018 (English Translation).
Office Action pertaining to U.S. Appl. No. 15/866,800 dated Jun. 19, 2018.
Office Action pertaining to U.S. Appl. No. 15/190,981 dated Apr. 4, 2017.
Office Action pertaining to U.S. Appl. No. 15/866,772 dated Aug. 28, 2018.
Harmse et al., "On the Product Formation in 1-Butene Methathesis over Supported Tungsten Catalysts", Catal. Lett, vol. 137, pp. 123-131, Apr. 2010.
Shaikh et al., "Self-Methathesis of Butenes to Propylene", Catalysis in Petroleum Refining & Petrochemicals, pp. 1-6, Dec. 7-8, 2015.
Debecker et al., "Preparation of MoO3/siO2-Al2O3 methathesis catalysts via wet impregnation with different Mo precursors", Journal of Molecular Catalysis A: Chemical, 340, pp. 65-76, 2011.
Wu et al., "Investigation on acidity of zeolites bound with silica and alumina", Studies in Surface Science and Catalysis, 143, pp. 217-225, 2002.
Hu et al., "Highly active doped mesoporous KIT-6 catalysts for mathesis of 1-butene and ethene to propene: The influence of neiboring environment of W. species", Journal of Physical Chemistry, vol. 117, pp. 26385-26395, 2013.
Examination Report pertaining to GCC Application No. 2016/31672 dated Sep. 13, 2018.
Office Action dated Jan. 31, 2019 pertaining to U.S. Appl. No. 15/866,800, filed Jan. 10, 2018 (34 pg).
Notice of Allowance dated Mar. 5, 2019 pertaining to U.S. Appl. No. 15/866,772, filed Jan. 10, 2018.
Office Action dated Apr. 5, 2019 pertaining to U.S. Appl. No. 15/873,421, filed Jan. 17, 2018, 49 pgs.
Office Action dated Apr. 29, 2019 pertaining to U.S. Appl. No. 16/039,983, filed Jul. 19, 2018, 36 pgs.
Yuan Guimei et al., Machine translation of CN 104370676, Feb. 2015.
Office Action dated May 2, 2019 pertaining to U.S. Appl. No. 15/859,794, filed Jan. 2, 2018, 30 pgs.
Office Action dated May 2, 2019 pertaining to U.S. Appl. No. 16/156,634, filed Oct. 10, 2018, 32 pgs.
Office Action dated Nov. 20, 2019 pertaining to U.S. Appl. No. 16/156,634, filed Oct. 10, 2018, 37 pgs.

(56) References Cited

OTHER PUBLICATIONS

Notice of Allowance and Fee(s) Due dated May 15, 2019 pertaining to U.S. Appl. No. 16/156,616, filed Oct. 10, 2018, 35 pgs.
U.S. Office Action dated Jun. 14, 2019 pertaining to U.S. Appl. No. 15/866,800, filed Jan. 10, 2018, 38 pgs.
Decision of Rejection pertaining to Japanese Application No. 2017-567370 dated Sep. 4, 2019.
European Search Report for Application No. 19163840.2 dated Aug. 2, 2019.
Chinese Office Action for Application No. 201811179717.1 dated Jun. 13, 2019.
European Search Report for Application No. 16738274.6 dated Aug. 2, 2019.
Office Action dated Jun. 18, 2019 pertaining to Korean Patent Application No. 10-2018-7003251.
Office Action dated Mar. 30, 2019 pertaining to Japanese Patent Application No. 2017-567370.
Notice of Allowance and Fee(s) Due dated Aug. 29, 2019 pertaining to U.S. Appl. No. 15/859,794, filed Jan. 2, 2018, 22 pgs.
Notice of Allowance and Fee(s) Due dated Sep. 26, 2019 pertaining to U.S. Appl. No. 15/873,421, filed Jan. 17, 2018, 30 pgs.
Examination Report pertaining to GCC Application No. 2016/31673 dated Apr. 7, 2020.
Office Action pertaining to application No. CN201811179717.1 dated Mar. 17, 2020, 7 pgs.
Office Action pertaining to Application No. CN201680039097.4 dated Mar. 4, 2020, 7 pgs.
Search Report pertaining to Application No. CN201680039097.4 dated Feb. 25, 2020.
Office Action dated Dec. 17, 2019 pertaining to Chinese Patent Application No. 201680038823.0.
Office Action dated Oct. 25, 2019 pertaining to Japanese Patent Application No. 2017-568232.
Office Action dated Jan. 5, 2020 pertaining to GCC Patent Application No. 2016-37609.
International Search Report and Written Opinion pertaining to Application No. PCT/US2019/054378 dated Jan. 13, 2020.
International Search Report and Written Opinion pertaining to Application No. PCT/US2019/054377 dated Jan. 13, 2020.
Office Action pertaining to U.S. Appl. No. 15/866,800 dated Jan. 13, 2020.
Office Action pertaining to Korean Application No. 10-2019-7005618 dated Feb. 25, 2020.
Search Report and Written Opinion pertaining to Singapore Application No. 10201913486W dated Jul. 21, 2020.
U.S. Office Action dated Aug. 21, 2020 pertaining to U.S. Appl. No. 16/712,280, filed Dec. 12, 2019, 67 pgs.
U.S. Office Action dated Sep. 15, 2020 pertaining to U.S. Appl. No. 16/156,634, filed Oct. 10, 2018, 38 pgs.
U.S. Office Action dated Sep. 16, 2020 pertaining to U.S. Appl. No. 16/522,142, filed Jul. 25, 2019, 72 pgs.
Office Action dated May 27, 2020 pertaining to U.S. Appl. No. 16/156,616, filed Oct. 10, 2018, 31 pgs.
Office Action dated Jul. 24, 2020 pertaining to U.S. Appl. No. 15/866,800, filed Jan. 10, 2018, 51 pgs.
Notice of Allowance and Fee(s) Due dated Oct. 19, 2020 pertaining to U.S. Appl. No. 15/866,800, filed Jan. 10, 2018, 27 pgs.
Notice of Allowance and Fee(s) Due dated Nov. 23, 2020 pertaining to U.S. Appl. No. 16/156,616, filed Oct. 10, 2018, 29 pgs.

* cited by examiner

DUAL CATALYST PROCESSES AND SYSTEMS FOR PROPYLENE PRODUCTION

CROSS-REFERENCE TO RELATED APPLICATION

This application is a divisional application of U.S. patent application Ser. No. 15/866,772 filed Jan. 10, 2018, which claims the benefit of U.S. Provisional Application Ser. No. 62/448,495 filed Jan. 20, 2017.

TECHNICAL FIELD

Embodiments of the present disclosure generally relate to catalytic propylene production, and more specifically relate to converting butene to propylene.

BACKGROUND

In recent years, there has been a dramatic increase in the demand for propylene to feed the growing markets for polypropylene, propylene oxide, and acrylic acid. Currently, most of the propylene produced worldwide is a byproduct from steam cracking units which primarily produce ethylene, or a byproduct from fluid catalytic cracking (FCC) units, which primarily produce gasoline. These processes cannot respond adequately to a rapid increase in propylene demand.

Other propylene production processes contribute a relatively small amount of total propylene production. Among these processes are propane dehydrogenation (PDH), metathesis reactions requiring both ethylene and butene, high severity FCC, olefins cracking, and methanol to olefins (MTO) processes. However, propylene demand has exceeded ethylene and gasoline/distillate demand, and propylene supply has not kept pace with this increase in propylene demand.

SUMMARY

Accordingly, an ongoing need exists for improved processes for the selective production of propylene. Embodiments of the present disclosure are directed to propylene production from butenes by a multiple-stage catalyst system.

According to one or more embodiments, a process for producing propylene may comprise at least partially metathesizing butene in a metathesizing reaction zone that may comprise a metathesis catalyst to form a metathesis reaction product. The metathesis catalyst may comprise, consist of, or consist essentially of a mesoporous silica-alumina catalyst support impregnated with metal oxide having a mesoporous silica-alumina catalyst support that may comprise from 5 weight percent to 50 weight percent alumina. The process may also comprise at least partially cracking the metathesis reaction product in a cracking reaction zone that may comprise a cracking catalyst to form a cracking reaction product. The cracking catalyst may comprise, consist of, or consist essentially of a Mordenite Framework Inverted (MFI) structured silica-containing catalyst, and the cracking reaction product may comprise propylene.

According to another embodiment, a multiple-stage catalyst system for producing propylene from butene may comprise a metathesis reaction zone and a cracking reaction zone downstream of the metathesis reaction zone. The metathesis reaction zone may comprise a mesoporous silica-alumina catalyst support impregnated with metal oxide that may have a mesoporous silica-alumina catalyst support that comprises from 5 weight percent to 50 weight percent alumina. The cracking reaction zone may comprise a MFI structured silica-containing catalyst. The MFI structured silica-containing catalyst may crack a metathesis product stream to form a cracking product stream that may comprise propylene.

Additional features and advantages of the described embodiments will be set forth in the detailed description which follows, and in part will be readily apparent to those skilled in the art from that description or recognized by practicing the described embodiments, including the detailed description which follows, the claims, as well as the appended drawings.

BRIEF DESCRIPTION OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
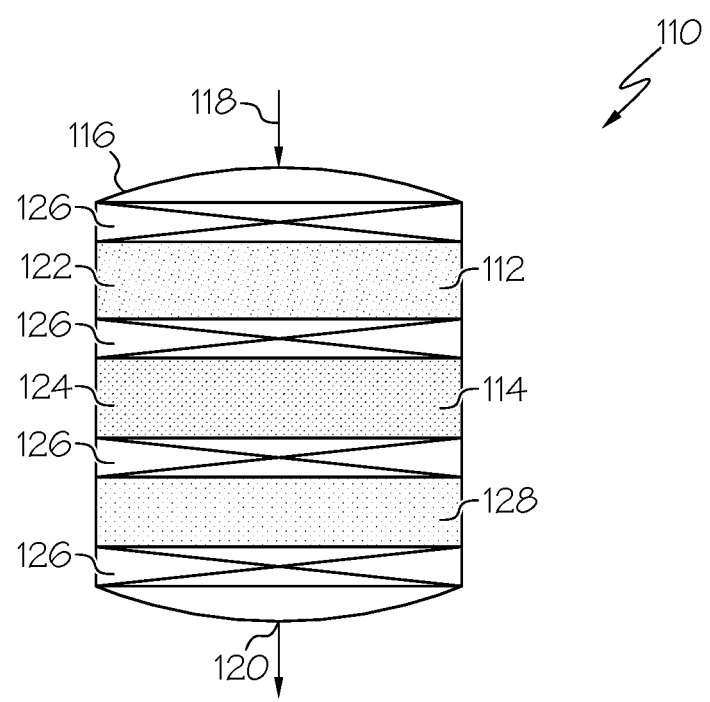
FIG. 1 schematically depicts a fixed bed continuous flow reactor including a metathesis reaction zone and a cracking reaction zone, according to one or more embodiments of the present disclosure.

Embodiments of the present disclosure are directed to systems and methods for converting a hydrocarbon stream containing butene to a stream comprising propylene by catalyzed metathesis and catalyzed cracking. Specifically, the present embodiments are related to multiple-stage (for example, dual-stage) catalyst systems containing metathesis and cracking catalysts for propylene production from a feed stream containing butene. While a dual-stage catalyst system with 2 catalysts is used throughout this disclosure for simplicity and clarity, it may be appreciated that the multiple-stage catalyst system may include more than 2 catalysts, such as 3 catalysts, 4 catalysts, 5 catalysts, or even more catalysts. In one or more embodiments, the metathesis catalyst is followed by the cracking catalyst (that is, in series). The metathesis catalyst may be a combination catalyst comprising a mesoporous silica-alumina catalyst support impregnated with metal oxide, which may provide an improved yield of propylene, and optionally an improved combined yield of propylene and ethylene as compared to other metathesis reaction systems.

The hydrocarbon stream which is introduced to the catalysts may be any stream comprising butene, which may include 1-butene, cis-2-butene, trans-2-butene, or combinations of these isomers. In one or more embodiments, the hydrocarbon stream comprising butene may be a raffinate stream created by a naphtha cracking process.

As used in this disclosure, a "reactor" refers to a vessel in which one or more chemical reactions may occur between one or more reactants optionally in the presence of one or more catalysts. For example, a reactor may include a tank or tubular reactor configured to operate as a batch reactor, a continuous stirred-tank reactor (CSTR), or a plug flow reactor. Example reactors include packed bed reactors, such as fixed bed reactors, and fluidized bed reactors. Example reactors may be oriented vertically, horizontally, or at an angle between vertical and horizontal. Example reactors may also be up flow or down flow reactors. A reaction system may include one or more "reaction zones." As used in this disclosure, a "reaction zone" refers to an area where a particular reaction takes place. For example, a packed bed reactor with multiple catalyst beds may have multiple reaction zones, where each reaction zone is defined by the volume of each catalyst bed. In another non-limiting example, a multiple-stage catalyst reaction system may include multiple reactors, and each reactor may define a separate "reaction zone."

In one or more embodiments of a multiple-catalyst reaction system, a catalyst in each reaction zone may have a relatively small amount of different types of catalysts from the other reaction zones. For example, the reaction zone may have less than 10 weight percent (wt. %) of the catalyst from another reaction zone, or even less than 5 wt. % of the catalysts from another reaction zone.

As used in this disclosure, "cross-metathesis" refers to an organic reaction that involves the redistribution of fragments of alkenes by the scission and regeneration of carbon-carbon double bonds. Cross-metathesis may be achieved as shown in Chemical Formula 2, provided subsequently in the present disclosure, with the metathesis catalyst. In the case of 2-butene and 1-butene, the redistribution of these carbon-carbon double bonds through metathesis produces propylene and $C_5$-$C_6$ olefins. A "metathesis catalyst," as used in this disclosure, refers to a catalyst that promotes the metathesis reaction of alkenes to form other alkenes. The metathesis catalyst may also convert 2-butene to 1-butene through isomerization, which is shown in Chemical Formula 1 subsequently provided in this disclosure. Isomerization of 2-butene to 1-butene, and vice versa, by the metathesis catalyst may be an equilibrium reaction as denoted by, the bi-directional arrows with single heads. Further, "catalytic cracking" refers to the catalytic conversion of $C_4$-$C_6$ alkenes to propylene and other alkanes, alkenes, or alkanes and alkenes, for example, $C_1$-$C_2$ alkenes. As shown in Chemical Formula 3, "catalytic cracking" includes conversion of pentenes, $C_{6+}$ alkenes, and unconverted butenes from the metathesis reaction to propylene, ethylene, and some higher hydrocarbons depending on the cracking conditions. Though not shown in Chemical Formula 3, light gases may also be produced by the cracking reactions.

Chemical Formula 1: Isomerization of 2-Butene to 1-Butene

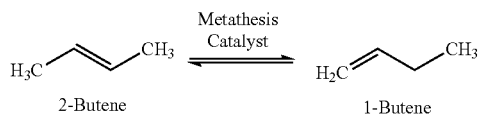

Chemical Formula 2: Cross-Metathesis

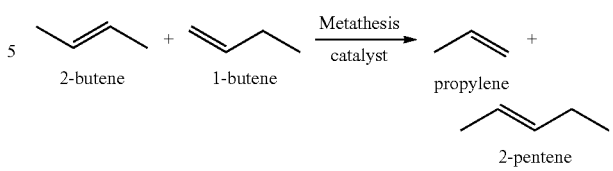

Chemical Formula 3: Catalytic Cracking

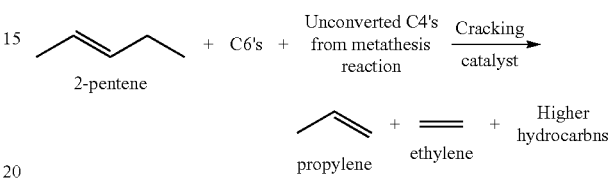

Referring to Chemical Formulas 1-3, the isomerization, cross-metathesis, and cracking reactions are not limited to these reactants and products; however, Chemical Formulas 1-3 provide a simplified illustration of the reaction methodology. As shown in Chemical Formula 2, metathesis reactions may take place between two alkenes. The groups bonded to the carbon atoms of the carbon-carbon double bond may be exchanged between the molecules to produce two new alkenes with the exchanged groups. The specific catalyst that is selected for the olefin metathesis reaction may generally determine whether a cis-isomer or trans-isomer is formed, as the formation of a cis- or trans-isomer may be a function at least partially of the coordination of the olefin molecules with the catalyst, as may be the steric influences of the substituents on the carbon-carbon double bond of the newly formed molecule. Although cross-metathesis of 1-butene and 2-butene to propylene and 2-pentene is shown in Chemical Formula 2, it is understood that other secondary cross-metathesis reactions or self-metathesis reactions may occur between one or more alkenes in the reactions streams.

In operation, a product stream comprising propylene may be produced from a stream containing butene through metathesis conversion and cracking by contacting the stream containing butene with the multiple-stage catalyst system comprising a combination metathesis catalyst and a cracking catalyst. The stream containing butene may include 2-butene, which may include isomers cis-2-butene, trans-2-butene, or both. The stream containing butene may optionally include 1-butene. The present disclosure focuses, in some embodiments, on streams containing 2-butene, 1-butene, or both; however, it is known that other $C_1$-$C_6$ components may also be present in the stream containing butene.

Referring to FIG. 1, an embodiment of the multiple-stage catalyst system for producing propylene from an inlet stream containing butene is illustrated, the multiple-stage catalyst system being designated by reference number 110. The multiple-stage catalyst system 110 may include a metathesis reaction zone 112 and a cracking reaction zone 114. The cracking reaction zone 114 may be positioned downstream of the metathesis reaction zone 112. In one or more embodiments, the multiple-stage catalyst system 110 may include a reactor 116. As depicted in FIG. 1, an inlet stream 118 is introduced to the reactor 116, and an outlet stream 120 passes out of the reactor 116. In some embodiments, the multiple-stage catalyst system 110 may comprise the metathesis reaction zone 112 and the cracking reaction zone 114 disposed within the reactor 116. Thus, reactant contents are introduced to the metathesis reaction zone 112 via the inlet stream 118, pass through the metathesis reaction zone 112 and the cracking reaction zone 114, and then pass out of the cracking reaction zone 114 as the outlet stream 120.

While not depicted in FIG. 1, it should be understood that in other embodiments, each reaction zone (that is, the metathesis reaction zone 112, the cracking reaction zone 114, and any other reaction zones that may be included in the multiple-stage catalyst system) may be disposed in its own separate reactor, and the reactors for each reaction zone may be arranged in series. In one or more embodiments, two reactors may be arranged in series, where the effluent of the upstream reactor enters the downstream reactor in an inlet stream. The upstream reactor may include the metathesis reaction zone 112, and the downstream reactor may include the cracking reaction zone 114. Each of the upstream reactor and downstream reactor may include one or more supplemental reaction zones in addition to the metathesis reaction zone 112 and cracking reaction zone 114 respectively.

As described previously in this disclosure, 2-butene (including isomers cis-2-butene, trans-2-butene, or both) may be present in the inlet stream 118. The inlet stream 118 may include from 10 wt. % to 70 wt. %, from 10 wt. % to 60 wt. %, from 10 wt. % to 50 wt. %, from 10 wt. % to 40 wt. %, from 20 wt. % to 70 wt. %, from 20 wt. % to 60 wt. %, from 20 wt. % to 50 wt. %, from 20 wt. % to 40 wt. %, from 30 wt. % to 70 wt. %, from 30 wt. % to 60 wt. %, from 30 wt. % to 50 wt. %, from 30 wt. % to 40 wt. %, or from 10 wt. % to 30 wt. % 2-butene. The inlet stream may also include 1-butene. In some embodiments, the inlet stream 118 may include from 5 wt. % to 60 wt. %, from 5 wt. % to 50 wt. %, from 5 wt. % to 40 wt. %, from 10 wt. % to 60 w. %, from 10 wt. % to 50 wt. %, from 10 wt. % to 40 wt. %, from 15 wt. % to 60 wt. %, from 15 wt. % to 50 wt. %, from 15 wt. % to 40 wt. %, from 5 wt. % to 20 wt. %, or from 40 wt. % to 60 wt. % 1-butene. The inlet stream 118 may also include n-butane. In some embodiments, the inlet stream 118 may include from 5 wt. % to 30 wt. %, from 10 wt. % to 30 wt. %, from 15 wt. % to 30 wt. %, from 5 wt. % to 25 wt. %, from 10 wt. % to 25 wt. %, from 15 wt. % to 25 wt. %, from 5 wt. % to 15 wt. %, or from 25 wt. % to 30 wt. % n-butane.

The inlet stream 118 may be a raffinate stream from a petrochemical refinery process. In example multiple-stage catalyst systems 110, the inlet stream 118 may be a raffinate stream from a fluidized catalytic cracking (FCC) reactor system or an ethylene cracking reactor system. In an example multiple-stage catalyst system 110, the inlet stream 118 may be a raffinate-2 stream produced from an FCC reactor, the raffinate-2 stream including from 20 wt. % to 60 wt. % of cis- or trans-2-butene, or both, from 10 wt. % to 20 wt. % of 1-butene, and from 5 wt. % to 20 wt. % n-butane. In another example multiple stage catalyst system 110, the inlet stream 118 may be a raffinate-2 stream produced from an ethylene cracking reactor, the raffinate-2 stream including 20 wt. % to 30 wt. % of cis- or trans-2-butene, or both, from 40 wt. % to 60 wt. % 1-butene, and from 10 wt. % to 20 wt. % of n-butane. In still other example multiple stage catalyst systems 110, the inlet stream 118 may be a raffinate-3 stream that may include from 30 wt. % to 70 wt. % of cis- or trans-2-butene and from 10 wt. % to 30 wt. % of n-butane. In one or more example multiple stage catalyst system 110, the inlet stream 118 may be a raffinate-1 stream that includes from 10 wt. % to 30 wt. % of cis- or trans-2-butene, or both, from 25 wt. % to 50 wt. % of 1-butene, and from 20 wt. % to 50 wt. % isobutene. In one or more embodiments, the inlet stream 118 containing butene may be substantially free of ethylene. As used in this disclosure, the term "substantially free" of a component means less than 1 wt. % of that component in a particular portion of a catalyst, stream, or reaction zone. As an example, the inlet stream 118, which is substantially free of ethylene, may have less than 1 wt. % of ethylene. In one or more embodiments, the inlet stream 118 containing butene may be substantially free of isobutene. In one or more embodiments, the inlet stream 118 containing butene may have less than 0.1 wt. % of isobutene. In one or more examples of the multiple stage catalyst system 110, the inlet stream 118 containing butene may be a raffinate-1 stream having from 20 wt. % to 50 wt. % isobutene.

The metathesis reaction zone 112 may include a metathesis catalyst 122. In the metathesis reaction zone 112, the metathesis catalyst 122 may convert 1-butene and 2-butene, to propylene and other alkenes through cross-metathesis. The metathesis reaction zone 112 may produce a metathesis reaction product that may include propylene and other alkanes and alkenes, such as pentene and other $C_5+$ olefins, for example. The metathesis reaction product may also include unreacted butenes, such as cis-2-butene, trans-2-butene, 1-butene, or combinations of two or more of these butenes. The metathesis catalyst 122 may also isomerize a portion of the 2-butene to 1-butene, and vice versa, in the metathesis reaction zone 112. Isomerization of 2-butene to 1-butene, and vice versa, with the metathesis catalyst 122 in the metathesis reaction zone 112 may be an equilibrium reaction and may operate to maintain equilibrium concentrations of 2-butene and 1-butene in the metathesis reaction zone 112 to provide adequate concentrations of both 2-butene and 1-butene as reactants for the cross-metathesis reaction. In one or more embodiments, isomerization of 2-butene to 1-butene may occur through self-metathesis. In one or more embodiments, the metathesis catalyst 122 may include a mesoporous silica-alumina catalyst support impregnated with a metal oxide.

The cracking reaction zone 114 of the multiple-stage catalyst system 110 may include a cracking catalyst 124 that may convert at least a portion of the unreacted 2-butene and the produced $C_5+$ olefins in the metathesis reaction product stream, which are produced in the metathesis reaction zone 112, to lighter olefins, such as ethylene and propylene. Thus, the cracking reaction zone 114 may produce a cracking reaction product that may include propylene, ethylene, or both. The cracking reaction product may be passed out the cracking reaction zone 114 in the outlet stream 120. Other $C_4+$ hydrocarbons, such as butane or pentane that may be present in the metathesis reaction product stream, may also be converted to lighter alkanes and alkenes by the cracking catalyst 124 in the cracking reaction zone 114. In one or more embodiments, the cracking catalyst 124 may comprise, consist of, or consist essentially of a MFI structured silica-containing catalyst. In one or more embodiments, the cracking catalyst 124 may be a zeolite catalyst.

In one or more embodiments, the multiple-stage catalyst system 110 for producing propylene from butene may comprise a metathesis reaction zone 112 and a cracking reaction zone 114 downstream of the metathesis reaction zone 112. The metathesis reaction zone 112 may comprise, consist of, or consist essentially of a mesoporous silica-alumina catalyst support impregnated with metal oxide having a mesoporous silica-alumina catalyst support that comprises from 5 weight percent to 50 weight percent alumina. The cracking reaction zone 114 may comprise, consist of, or consist essentially of a MFI structured silica-containing catalyst, where the MFI structured silica-containing catalyst cracks a metathesis product stream to form a cracking product stream comprising propylene.

Referring to FIG. 1, in one or more embodiments, the metathesis reaction zone 112 and the cracking reaction zone 114 may be disposed in the reactor 116 with the metathesis reaction zone 112 positioned next to or towards the inlet stream 118 of the reactor 116 and the cracking reaction zone 114 positioned downstream of the metathesis reaction zone 112. In one or more embodiments, the inlet stream 118 may feed directly into the metathesis reaction zone 112. One or more additional reaction zones (not shown) may be disposed within the reactor 116 upstream or downstream of one or both of the metathesis reaction zone 112 or the cracking reaction zone 114. As indicated previously in this disclosure, the discussion of a multiple-stage catalyst system having two reaction zones is merely for simplicity and a multiple-stage catalyst system with three or more reaction zones and three or more catalysts is also envisioned.

Optionally, a separator 126 may be placed between the metathesis reaction zone 112 and the cracking reaction zone 114 to maintain the metathesis catalyst 122 in the metathesis reaction zone 112 and the cracking catalyst 124 in the cracking reaction zone 114. The separator 126 may be porous to allow materials, such as the metathesis reaction product, to flow through the separator 126. The separator 126 may be chemically inert and generally makes no contribution to the reaction chemistry. The separator 126 inert material such as silicon carbide, glass, stainless steel, ceramics, quartz, or other chemically inert material. The packing material 128 may be spheres, rings, cylinders, springs, wools or other fabrics, granules, pellets, or combinations of these. In one or more embodiments, the separator 126 may be a quartz wool separator. Separators 126 may optionally be placed between the metathesis reaction zone 112 or the cracking reaction zone 114 and any other reaction zone. The separators 126 may also optionally be positioned between the inlet stream 118 and one of the reaction zones and between the outlet stream 120 and one of the reaction zones.

In one or more embodiments, a separator 126 may be positioned between the metathesis reaction zone 112 and the cracking reaction zone 114. Inserting the separator 126 between the metathesis reaction zone 112 and the cracking reaction zone 114 may generally maintain the metathesis catalyst 122 in the metathesis reaction zone 112 and maintain the cracking catalyst 124 in the cracking reaction zone 114. Maintaining the catalysts 122, 124 in their respective reaction zones 112, 114 may prevent migration of the catalysts 122, 124 between reaction zones, which may lead to increased production of undesired byproducts and decreased yield. In one or more embodiments, each of the metathesis reaction zone 112 and the cracking reaction zone 114 may have a relatively small amount of the different types of catalysts from other reaction zones. For example, the metathesis reaction zone 112 may comprise less than 10 wt. % of the cracking catalyst 124 from the cracking reaction zone 114, or even less than 5 wt. % of the cracking catalyst 124 from the cracking reaction zone 114. Additionally, the cracking catalyst zone 114 may comprise less than 10 wt. % of the metathesis catalyst 122 from the metathesis reaction zone 112, or even less than 5 wt. % of the metathesis catalyst 122 from the metathesis reaction zone 112. In some embodiments, each reaction zone 112, 114 may be substantially free of different types of catalysts from other reaction zones so that each reaction zone 112, 114 may contain less than 1 wt. % of different types of catalysts from other reaction zones. In other embodiments, the metathesis reaction zone 112 may be positioned directly against the cracking reaction zone 114 without an intervening separator 126 positioned between the two reaction zones 112, 114.

An optional layer of packing material 128 may be positioned downstream of the cracking reaction zone 114, between the cracking reaction zone 114 and the outlet stream 118. The packing material 128 may be chemically inert and generally makes no contribution to the reaction chemistry. The packing material 128 may also be porous to allow the cracking reaction product to penetrate through the packing material 128 from the cracking reaction zone 114 to the outlet stream 120, but may provide a barrier to retain the catalysts within the reactor. The packing material 128 may be a chemically inert material such as silicon carbide, glass, stainless steel, ceramics, or other chemically inert material. The packing material 128 may be spheres, rings, cylinders, springs, granules, pellets, other shapes, or combinations of these. The packing material 128 may provide an inert support for the catalysts and may additionally aid in maintaining constant flow of reactants through the multiple stage catalyst system 110 while minimizing a generation of hot spots.

As described previously in this disclosure, the metathesis catalyst 122 may be a combination metathesis catalyst such as a mesoporous silica-alumina catalyst support impregnated with a metal oxide. The mesoporous silica-alumina catalyst support impregnated with metal oxide may comprise a mesoporous silica-alumina catalyst support. As used in this disclosure, the term "mesoporous silica-alumina catalyst support," when used by itself, refers to the silica-alumina catalyst support without the impregnated metal oxide. The mesoporous silica-alumina catalyst support may comprise a composition that includes both silica and alumina. Various materials are contemplated for the mesoporous silica-alumina catalyst support, for example, one or more molecular sieves or zeolites.

The mesoporous silica-alumina catalyst support may include from 5 weight percent (wt. %) to 50 wt. %, from 5 wt. % to 45 wt. %, from 5 wt. % to 40 wt. %, from 5 wt. % to 35 wt. %, from 5 wt. % to 30 wt. %, from 10 wt. % to 50 wt. %, from 10 wt. % to 45 wt. %, from 10 wt. % to 40 wt. %, from 10 wt. % to 35 wt. %, from 10 wt. % to 30 wt. %, from 15 wt. % to 50 wt. %, from 15 wt. % to 45 wt. %, from 15 wt. % to 40 wt. %, from 15 wt. % to 35 wt. %, from 15 wt. % to 30 wt. %, from 20 wt. % to 50 wt. %, from 20 wt. % to 45 wt. %, from 20 wt. % to 40 wt. %, from 20 wt. % to 35 wt. %, from 20 wt % to 30 wt. %, from 5 wt. % to 10 wt. %, from 10 wt. % to 15 wt. %, from 15 wt. % to 20 wt. %, from 30 wt. % to 35 wt. %, from 35 wt. % to 40 wt. %, from 40 wt. % to 45 wt. %, from 45 wt. % to 50 wt. %, from 5 wt. % to 15 wt. %, from 5 wt. % to 20 wt. %, from 10 wt. % to 20 wt. %, from 30 wt. % to 50 wt. %, from 30 wt. % to 45 wt. %, from 30 wt. % to 40 wt. %, or from 35 wt. % to 50 wt. % alumina. The weight percent of alumina is calculated based on a unit weight of the mesoporous silica-alumina catalyst support without the impregnated metal oxide. In one or more embodiments, the weight percent of alumina in the mesoporous silica-alumina catalyst support may be from 5 wt. % to 50 wt. %. In one or more embodiments, the mesoporous silica-alumina catalyst support may comprise from 10 wt. % to 40 wt. % alumina. In one or more embodiments, the mesoporous silica-alumina catalyst support may comprise from 20 wt. % to 30 wt. % alumina.

The mesoporous silica-alumina catalyst support, without the impregnated metal oxide, may include from 50 wt. % to 95 wt. %, from 50 wt. % to 90 wt. %, from 50 wt. % to 85 wt. %, from 50 wt. % to 80 wt. %, from 55 wt. % to 95 wt. %, from 55 wt. % to 90 wt. %, from 55 wt. % to 85 wt. %, from 55 wt. % to 80 wt. %, from 60 wt. % to 95 wt. %, from 60 wt. % to 90 wt. %, from 60 wt. % to 85 wt. %, from 60 wt. % to 80 wt. %, from 65 wt. % to 95 wt. %, from 60 wt. % to 90 wt. %, from 60 wt. % to 85 wt. %, from 60 wt. % to 80 wt. %, from 65 wt. % to 95 wt. %, from 65 wt. % to 90 wt. %, from 65 wt. % to 85 wt. %, from 65 wt. % to 80 wt. %, from 70 wt. % to 95 wt. %, from 70 wt. % to 90 wt. %, from 70 wt. % to 85 wt. %, from 70 wt. % to 80 wt. %, from 90 wt. % to 95 wt. %, from 85 wt. % to 90 wt. %, from 80 wt. % to 85 wt. %, from 80 wt. % to 95 wt. %, from 80 wt. % to 90 wt. %, from 85 wt. % to 95 wt. %, from 50 wt. % to 60 wt. %, from 50 wt. % to 65 wt. %, from 50 wt. % to 70 wt. %, from 55 wt. % to 70 wt. %, from 55 wt. % to 65 wt. %, or from 55 wt. % to 60 wt. % silica. The weight percent of silica is calculated based on the weight of the mesoporous silica-alumina catalyst support without the impregnated metal oxide. In one or more embodiments, the mesoporous silica-alumina catalyst support may comprise from 50 wt. % to 95 wt. % silica. In one or more embodiments, the mesoporous silica-alumina catalyst support may comprise from 10 wt. % to 90 wt. % silica. In one or more embodiments, the mesoporous silica-alumina catalyst support may comprise from 70 wt. % to 80 wt. % silica.

The ratio of silica to alumina in the mesoporous silica-alumina catalyst support may be varied to provide differing surface area and pore volume, which may influence the yield, conversion, and selectivity of the multiple-stage catalyst system. The mesoporous silica-alumina catalyst support may have a weight ratio of alumina to silica of from 50:50 to 5:95, from 50:50 to 10:90, from 50:50 to 15:85, from 50:50 to 20:80, from 50:50 to 25:75, from 45:55 to 5:95, from 45:55 to 10:90, from 45:55 to 15:85, from 45:55 to 20:80, from 45:55 to 25:75, from 40:60 to 5:95, from 40:60 to 10:90, from 40:60 to 15:85, from 40:60 to 20:80, from 40:60 to 25:75, from 35:65 to 5:95, from 35:65 to 10:90, from 35:65 to 15:85, from 35:65 to 20:80, from 35:65 to 25:75, from 30:70 to 5:95, from 30:70 to 10:90, from 30:70 to 15:85, from 30:70 to 20:80, from 25:75 to 5:95, from 25:75 to 10:90, from 25:75 to 15:85, from 20:80 to 5:95, from 20:80 to 10:90, from 15:85 to 5:95, from 50:50 to 30:70, from 50:50 to 35:65, from 50:50 to 40:60, from 45:55 to 35:65, from 45:55 to 30:70, or from 40:60 to 30:70. In one or more embodiments, the mesoporous silica-alumina catalyst support may have a weight ratio of alumina to silica of from 1:99 to 15:85, or from 2:98 to 10:90 in other embodiments, or from 2:98 to 8:12 in yet other embodiments, or from 3:97 to 7:93 in still other embodiments.

Combining silica and alumina in the mesoporous silica-alumina catalyst support impregnated with metal oxide may increase the isomerization of 2-butene in the butene containing inlet stream to 1-butene as compared to a metathesis catalyst containing only silica. Increasing the isomerization of 2-butene to 1-butene may increase the availability of 1-butene so that sufficient quantities of both 2-butene and 1-butene are available to undergo further conversion to propylene and other alkenes through cross-metathesis by the mesoporous silica-alumina catalyst support impregnated with metal oxide. This may result in increased concentrations of propylene, ethylene, and other $C_5+$ alkenes in the metathesis reaction product and overall increased yield, conversion, and propylene selectivity of the multiple-stage catalyst system 110. The yield, conversion, and propylene selectivity of the multiple-stage catalyst system 110 with a metathesis catalyst 122 containing alumina and silica may be greater than the yield, conversion, and propylene selectivity of multiple-stage catalyst systems utilizing a metathesis catalyst containing silica with no alumina.

Metathesis of butene in the butene-containing inlet stream 118 to propylene and other alkenes in a metathesis reaction product stream may be conducted over a broad range of temperatures. By using the mesoporous silica-alumina catalyst support impregnated with metal oxide that includes both silica and alumina in the mesoporous catalyst support, the metathesis reaction of butene to propylene in the metathesis reaction zone 112 may be conducted at a lesser operating temperature while producing acceptable yields of propylene and ethylene and decreasing unwanted side reactions that produce undesired byproducts as compared to a multiple-stage catalyst system having a silica-based metathesis catalyst with no alumina. Without wishing to be bound by theory, it is believed that the combination of alumina and silica in the mesoporous silica-alumina catalyst support impregnated with metal oxide is capable of isomerizing 2-butene to 1-butene at a lesser reaction temperature than a mesoporous silica metathesis catalyst having no alumina or other metathesis catalysts. The lesser reactor operating temperature allowed by the mesoporous silica-alumina catalyst support impregnated with metal oxide may further increase propylene yield, conversion, and propylene selectivity of the multi-stage catalyst system 110. A lesser operating temperature may also decrease energy costs for providing additional heating, which may reduce the operating costs of the multiple-stage catalyst system 110, among other benefits. Although the present disclosure describes the mesoporous silica-alumina catalyst support impregnated with metal oxide as being functional to metathesize 2-butene to propylene to isomerize 2-butene to 1-butene and vice versa, it is understood that the mesoporous silica-alumina catalyst support impregnated with metal oxide may have one or more other additional functionalities.

As used in the present disclosure, "mesoporous" refers to a material having an average pore size of greater than 2 nanometers and less than 50 nanometers. The average pore size may be obtained from the average surface area and pore size distribution, which are determined using the BET method subsequently described in this disclosure. Average pore size is generally determined as a pore diameter or pore radius based on the assumption of cylindrical shaped pores. However, it is understood that catalysts described in this disclosure may have actual shapes that are cylindrical or other shapes, such as, but not limited to, conical, square, slit-shaped, or other irregular shaped pores or combinations of these. In this disclosure, the average pore size is reported as an average pore diameter. The mesoporous silica catalyst support impregnated with metal oxide may have a relative pore volume per weight of material of at least 0.6 cubic centimeters per gram ($cm^3/g$). Without being bound by theory, the present pore size distribution and pore volume of the mesoporous silica-alumina catalyst support impregnated with metal oxide may be sized to achieve better catalytic activity and reduced blocking of pores by metal oxides, whereas smaller pore volume and pore size catalyst systems may be susceptible to pore blocking and thereby reduced catalytic activity.

In one or more embodiments, the average pore size of the mesoporous silica-alumina catalyst support impregnated with metal oxide may be from 2 nanometers (nm) to 50 nm, from 2.5 nm to 40 nm, from 2.5 nm to 30 nm, from 2.5 nm to 20 nm, from 2.5 nm to 18 nm, from 2.5 nm to 12 nm, from 2.5 nm to 4.5 nm, from 2.5 nm to 3.5 nm, from 8 nm to 12 nm, from 8 nm to 18 nm, from 8 nm to 20 nm, from 8 nm to 40 nm, from 12 nm to 18 nm, or from 12 nm to 40 nm.

In one or more embodiments, the relative pore volume per weight of the mesoporous silica-alumina catalyst support impregnated with metal oxide may be from 0.6 centimeters cubed per gram ($cm^3/g$) to 2.5 $cm^3/g$, from 0.6 $cm^3/g$ to 1.5 $cm^3/g$, from 0.6 $cm^3/g$ to 1.3 $cm^3/g$, from 0.6 $cm^3/g$ to 1.1 $cm^3/g$, from 0.6 $cm^3/g$ to 0.9 $cm^3/g$, from 0.7 $cm^3/g$ to 0.9 $cm^3/g$, from 0.7 $cm^3/g$ to 1.1 $cm^3/g$, from 0.7 $cm^3/g$ to 1.3 $cm^3/g$, from 0.7 $cm^3/g$ to 1.5 $cm^3/g$, from 0.7 $cm^3/g$ to 2.5 $cm^3/g$, from 0.8 $cm^3/g$ to 1.3 $cm^3/g$, from 0.8 $cm^3/g$ to 1.5 $cm^3/g$, or from 0.8 $cm^3/g$ to 2.5 $cm^3/g$. In some embodiments, the mesoporous silica-alumina catalyst support impregnated with metal oxide may have a relative pore volume per weight of the mesoporous silica-alumina catalyst support impregnated with metal oxide of at least 0.6 $cm^3/g$.

Moreover, while broader ranges are contemplated, the mesoporous silica-alumina catalyst support impregnated with metal oxide, in one or more embodiments, may include a surface area per weight of the mesoporous silica-alumina catalyst support impregnated with metal oxide of from 200 meters squared per gram ($m^2/g$) to 600 $m^2/g$. In other embodiments, the mesoporous silica-alumina catalyst support impregnated with metal oxide may have a surface area from 200 $m^2/g$ to 350 $m^2/g$, from 200 $m^2/g$ to 325 $m^2/g$, from 200 $m^2/g$ to 300 $m^2/g$, from 225 $m^2/g$ to 600 $m^2/g$, from 225 $m^2/g$ to 350 $m^2/g$, from 225 $m^2/g$ to 325 $m^2/g$, from 225 $m^2/g$ to 300 $m^2/g$, from 250 $m^2/g$ to 600 $m^2/g$, from 250 $m^2/g$ to 350 $m^2/g$, from 250 $m^2/g$ to 325 $m^2/g$, from 250 $m^2/g$ to 300 $m^2/g$, from 300 $m^2/g$ to 325 $m^2/g$, or from 300 $m^2/g$ to 350 $m^2/g$.

The mesoporous silica-alumina catalyst support impregnated with metal oxide may have an mean particle size of from 20 nm to 200 nm, from 20 nm to 150 nm, from 20 nm to 100 nm, from 20 nm to 75 nm, from 50 nm to 200 nm, from 50 nm to 150 nm, from 50 nm to 125 nm, from 50 nm to 75 nm, from 75 nm to 200 nm, from 75 nm to 150 nm, or from 75 nm to 125 nm. The mesoporous silica-alumina catalyst support impregnated with metal oxide may have a mean particle size distribution of from 100 Angstroms (Å) to 300 Å, from 100 Å to 250 Å, from 100 Å to 200 Å, from 120 Å to 300 Å, from 120 Å to 250 Å, and from 120 Å to 200 Å. The mean particle size and mean particle size distribution can be measured using a particle size analyzer, such as a Nanopartica™ series particle size analyzer from Horiba Scientific Company, which measures the size of single particles dispersed in water using ultraviolet (UV) light.

Addition of the alumina to the mesoporous silica-alumina catalyst support may change the Brønsted acidity of the mesoporous silica-alumina catalyst support impregnated with metal oxide as compared to a mesoporous silica metathesis catalyst impregnated with metal oxide with no alumina. The acidity of the mesoporous silica-alumina catalyst support impregnated with metal oxide may be influence by the proportion of alumina incorporated into the catalyst support as well as the type of alumina utilized. The mesoporous silica-alumina catalyst support impregnated with metal oxide may have a total acidity from 0.001 millimole/gram (mmol/g) to 0.5 mmol/g, from 0.01 mmol/g to 0.5 mmol/g, from 0.1 mmol/g to 0.5 mmol/g, from 0.3 mmol/g to 0.5 mmol/g, from 0.4 mmol/g to 0.5 mmol/g, from 0.001 mmol/g to 4 mmol/g, or from 0.001 mmol/g to 0.3 mmol/g. The acidity may be generally maintained at or less than 0.5 mmol/g, which may result in an acceptable propylene selectivity of the multiple-stage catalyst system 110 and a reduction in production of undesirable byproducts, such as aromatics. Increasing acidity of the mesoporous silica-alumina catalyst support impregnated with metal oxide may increase the overall butene conversion; however, this increased conversion may lead to decreased propylene selectivity and increased production of aromatic byproducts, which may lead to catalyst coking and deactivation.

Incorporation of the alumina into the mesoporous silica-alumina catalyst support impregnated with metal oxide may further modify the interaction between the mesoporous silica-alumina catalyst support and the metal oxide impregnated on the catalyst support. Not to be limited by theory, the introduction of alumina into the mesoporous catalyst support may increase the number of surface hydroxyl groups, which may facilitate dispersion of the metal oxide on the silica-alumina surface. Thus, inclusion of the alumina in the mesoporous silica-alumina catalyst support may contribute to higher dispersion of the metal oxide, such as tungsten oxide, on the surface of the silica-alumina catalyst support. Additionally, the hydroxyl groups may facilitate coupling the metal oxide to the surface of the silica-alumina support, which may reduce or eliminate sintering of the metal oxide to the surface of the silica-alumina catalyst support.

For the mesoporous silica-alumina catalyst support impregnated with metal oxide, the metal oxide may include one or more oxides of a metal from Groups 6-10 of the IUPAC Periodic Table. In some embodiments, the metal oxide may include one or more oxides of molybdenum, rhenium, tungsten, or any combination of these. In one or more embodiments, the metal oxide of the mesoporous silica-alumina catalyst support impregnated with metal oxide is tungsten oxide ($WO_3$). It is contemplated that various amounts of metal oxide may be impregnated into the mesoporous silica-alumina catalyst support. In some embodiments, the mesoporous silica-alumina catalyst support impregnated with metal oxide includes from 1 wt. % to 30 wt. %, from 1 wt. % to 25 wt. %, from 1 wt. % to 20 wt. %, from 1 wt. % to 15 wt. %, from 5 wt. % to 30 wt. %, from 5 wt. % to 25 wt. %, from 5 wt. % to 20 wt. %, from 5 wt. % to 15 wt. %, from 8 wt. % to 30 wt. %, from 8 wt. % to 25 wt. %, from 8 wt. % to 20 wt. %, from 8 wt. % to 15 wt. %, from 8 wt. % to 12 wt. %, from 10 wt. % to 30 wt. %, or from 10 wt. % to 20 wt. % metal oxide, for example tungsten oxide ($WO_3$), based on the total weight of the mesoporous silica-alumina catalyst support impregnated with metal oxide. In some embodiments, the mesoporous silica-alumina catalyst support impregnated with metal oxide includes from 1 wt. % to 30 wt. % tungsten oxide. In some embodiments, the mesoporous silica-alumina catalyst support impregnated with metal oxide includes from 5 wt. % to 20 wt. % tungsten oxide. In some embodiments, the mesoporous silica-alumina catalyst support impregnated with metal oxide includes from 8 wt. % to 12 wt. % tungsten oxide.

Various silica-containing structures are contemplated for the cracking catalyst. The cracking catalyst may be a zeolite. In one or more embodiments, the cracking catalyst may be a structured zeolite, such as MFI or BEA structured zeolite, for example. In one or more embodiments, the cracking catalyst may be a MCM-41 catalyst or a SBA-15 catalyst. In one or more embodiments, the cracking catalyst may be a MFI structured silica-containing catalyst. For example, the MFI structured silica-containing catalyst may include MFI structured aluminosilicate zeolite catalysts or MFI structured silica catalysts that do not contain alumina or are substantially free of alumina. In one or more embodiments, the MFI structured silica-containing catalyst is substantially free of alumina, having less than 1 wt. % alumina. In one or more embodiments, the MFI structured silica-containing catalysts may have less than 0.01 wt. % of alumina. In some embodiments, the MFI structured silica-containing catalyst may include greater than 0.01 wt. % alumina. Moreover, it is contemplated that the MFI structured silica-containing catalyst may include other impregnated metal oxides in addition to or as an alternative to alumina. The MFI structured silica-containing catalysts may have alumina, metal oxides, or both impregnated in the silica support. In addition to or as a substitute for alumina, it is contemplated that the MFI structured silica-containing catalyst may include one or more of the metal oxides previously listed in this disclosure, specifically, one or more oxides of a metal from Groups 6-10 of the IUPAC Periodic Table, more specifically, metal oxides of molybdenum, rhenium, tungsten, titanium, or combinations of these. It should be understood that the cracking catalyst may include a combination of multiple zeolites, such as zeolite particles which include multiple types of zeolites, or a mixture of zeolite particles where particles include different zeolites.

For MFI structured aluminosilicate zeolite catalysts, various amounts of alumina are contemplated. In one or more embodiments, the MFI structured aluminosilicate zeolite catalysts may have a molar ratio of silica to alumina of from 5 to 5000, from 5 to 4000, from 5 to 3000, from 5 to 2500, from 100 to 5000, from 100 to 4000, from 100 to 3000, from 100 to 2500, from 200 to 5000, from 200 to 4000, from 200 to 3000, from 200 to 2500, from 1000 to 5000, from 1000 to 4000, from 1000 to 3000, from 1000 to 2500, from 1500 to 5000, from 1500 to 4000, from 1500 to 3000, or from 1500 to 2500. Various suitable commercial embodiments of the MFI structured aluminosilicate zeolite catalysts are contemplated, for example, ZSM-5 zeolites such as MFI-280 produced by Zeolyst International or MFI-2000 produced by Saudi Aramco. Preparation of the MFI-2000 cracking catalyst is described subsequently in this disclosure in Example 5.

Various suitable commercial embodiments are also contemplated for the MFI structured silica-containing catalysts that are substantially free of alumina or have less than 0.01 wt. % alumina. One such example is Silicalite-1 produced by Saudi Aramco. Preparation of Silicalite-1 is subsequently described in this disclosure in Example 4.

The MFI structured silica-containing catalyst may include an average pore size of from 1.5 nm to 3 nm, or from 1.5 nm to 2.5 nm. Further, the MFI structured silica-containing catalyst may have an average relative pore volume per weight of material of from 0.1 cm$^3$/g to 0.3 cm$^3$/g, or from 0.15 cm$^3$/g to 0.25 cm$^3$/g. The MFI structured silica-containing catalyst may have an average surface area of from 300 m$^2$/g to 425 m$^2$/g, or from 340 m$^2$/g to 410 m$^2$/g. Additionally, the MFI structured silica-containing catalyst may have a total acidity of from 0.001 mmol/g to 0.1 mmol/g, or from 0.01 mmol/g to 0.08 mmol/g. The acidity may be maintained at or less than 0.1 mmol/g to reduce the production of undesirable byproducts, such as aromatic compounds. Increasing acidity may increase the amount of cracking; however, this increased cracking may also lead to less selectivity and increased production of aromatic byproducts, which may lead to catalyst coking and deactivation.

In some cases, the MFI structured silica-containing catalyst may be modified with an acidity modifier to adjust the level of acidity in the MFI structured silica-containing catalyst. For example, these acidity modifiers may include rare earth modifiers, phosphorus modifiers, potassium modifiers, or combinations thereof. Rare earth modifiers may be acidity modifiers comprising at least one rare earth metal selected from scandium, yttrium, and metals from the Lanthanide series (lutetium, lanthanum, cerium, praseodymium, neodymium, promethium, samarium, europium, gadolinium, terbium, dysprosium, holmium, erbium, thulium, and ytterbium) of the IUPAC periodic table. However, as the present embodiments are focused on reducing the acidity to a level at or less than 0.1 mmol/g, the present structured silica catalysts may have less than 0.01 wt. % acidity modifiers, such as those selected from rare earth modifiers, phosphorus modifiers, potassium modifiers, or combinations thereof.

Additionally, in some embodiments, the MFI structured silica-containing catalyst may have an individual crystal size of from 10 μm to 40 μm, from 15 μm to 40 μm, or from 20 μm to 30 μm. In other embodiments, the MFI structured silica-containing catalyst may have an individual crystal size of from 1 μm to 5 μm. Although the present disclosure describes the MFI structure silica-containing catalyst as being functional to crack $C_5+$ alkenes to propylene and other alkenes, it is understood that the MFI structured silica-containing catalysts may have one or more other additional functionalities.

Moreover, various amounts of each catalyst are contemplated for the present multiple-stage catalyst system 110. For example, it is contemplated that the ratio by volume of the metathesis catalyst 122 to the cracking catalyst 124 may be from 5:1 to 1:5, from 5:1 to 1:2, from 5:1 to 2:3, from 5:1 to 9:11, from 5:1 to 1:1, from 5:1 to 11:9, from 2:1 to 1:5, from 2:1 to 1:2, from 2:1 to 2:3, from 2:1 to 9:11, from 2:1 to 1:1, from 2:1 to 11:9, from 3:2 to 1:5, from 3:2 to 1:2, from 3:2 to 2:3, from 3:2 to 9:11, from 3:2 to 1:1, from 3:2 to 11:9, from 11:9 to 1:5, from 11:9 to 1:2, from 11:9 to 2:3, from 11:9 to 9:11, from 11:9 to 1:1, from 1:1 to 1:5, from 1:1 to 1:2, from 1:1 to 2:3, from 1:1 to 9:11, from 9:11 to 1:5, from 9:11 to 1:2, or from 9:11 to 2:3. In one or more embodiments, the volume ratio of the metathesis catalyst 122 in the metathesis reaction zone 112 to the cracking catalyst 124 in the cracking reaction zone 114 may be 1:1. In one or more embodiments, the volume ratio of the metathesis catalyst 122 in the metathesis reaction zone 112 to the cracking catalyst 124 in the cracking reaction zone 114 may be from 2:3 to 3:2. In one or more embodiments, the volume ratio of the metathesis catalyst 122 in the metathesis reaction zone 112 to the cracking catalyst 124 in the cracking reaction zone 114 may be from 9:11 to 11:9.

Various methods of making the metathesis catalyst 122 and cracking catalyst 124 used in the multiple-stage catalyst system 110 are contemplated and may be used. Specifically, the processes of wet impregnation and hydrothermal synthesis may be utilized; however, other catalyst synthesis techniques are also contemplated.

Referring again to FIG. 1, in a non-limiting example of a down flow reactor 116 in which the inlet stream 118 containing butene enters from the top of the reactor 116, the metathesis catalyst 122 may be located adjacent to or in a top part of the reactor 116, and the cracking catalyst 124 may be located in a middle or bottom part of the reactor 112. In other non-limiting examples, each catalyst may be positioned as discrete catalyst beds within the reactor 116. Moreover, it is contemplated that the metathesis catalyst 122 of the multiple-stage catalyst system 110 may be in contact with cracking catalyst 124 or may be separated by a separator 126 as previously described in this disclosure. However, if the metathesis catalyst 122 and cracking catalyst 124 are in contact, the metathesis catalyst 122 may still be disposed upstream of the cracking catalyst 124. It is contemplated that one or more additional catalysts may be used in conjunction with the metathesis catalyst 122 and cracking catalyst 124. In one embodiment, a guard catalyst bed (not shown) may be positioned upstream of the metathesis catalyst to remove contaminants from the butene containing inlet stream 118 entering the multiple-stage catalyst system 110.

Although depicted as a vertically-oriented down flow reactor in FIG. 1, the reactor 116 may also be an up flow reactor. Additionally, the reactor 116 may be oriented vertically, horizontally, or at an angle from 0 degrees (°) to 90° relative to the ground. For a reactor 116 oriented at an angle relative to the ground, the reactor 116 may be an up flow reactor in which the inlet stream 118 enters from a lower side of the reactor 116 and the outlet stream 120 exits from an upper side of the reactor 116, or the reactor 116 may be a down flow reactor in which the inlet stream 118 enters from the upper side of the reactor 116 and the outlet stream 120 exits from the lower side of the reactor.

It is contemplated that the metathesis catalyst 122 and the cracking catalyst 124 may be disposed in one reactor 116 or in multiple reactors. For example, separate reactors for the metathesis reaction zone 112 having the metathesis catalyst 122 and the cracking reaction zone 114 having the cracking catalyst 124 may be used when the metathesis reaction zone 112 and the cracking reaction zone 114 operate at different environmental conditions, including temperature and pressure. In one or more embodiments, the metathesis catalyst 122 may be disposed in a first reactor, and the cracking catalyst 124 may be disposed in a separate second reactor downstream of the first reactor. In one or more embodiments, direct conduits may extend between the first reactor and second reactor so that the cracking catalyst 124 may directly crack the metathesis reaction product stream, which is the product of the butene cross-metathesis reaction that occurs in the metathesis reaction zone 112.

Referring again to FIG. 1, various operating conditions are contemplated for contacting the stream containing butene with the multiple-stage catalyst system 110. For example, the stream containing butene (for example, the inlet stream 118) may contact the multiple-stage catalyst system 110 at a space hour velocity of from 10 per hour ($h^{-1}$) to 10,000 $h^{-1}$, from 10 $h^{-1}$ to 5000 $h^{-1}$, from 10 $h^{-1}$ to 2500 $h^{-1}$, from 10 $h^{-1}$ to 1200 $h^{-1}$, from 100 $h^{-1}$ to 10,000 $h^{-1}$, from 100 $h^{-1}$ to 5000 $h^{-1}$, from 100 $h^{-1}$ to 2500 $h^{-1}$, from 100 $h^{-1}$ to 1200 $h^{-1}$, from 300 $h^{-1}$ to 10,000 $h^{-1}$, from 300 $h^{-1}$ to 5000 $h^{-1}$, from 300 $h^{-1}$ to 2500 $h^{-1}$, from 300 $h^{-1}$ to 1200 $h^{-1}$, from 500 $h^{-1}$ to 10,000 $h^{-1}$, from 500 $h^{-1}$ to 5000 $h^{-1}$, from 500 $h^{-1}$ to 2500 $h^{-1}$, or from 500 $h^{-1}$ to 1200 $h^{-1}$.

The stream containing butene (for example, the inlet stream 118) may contact the multiple-stage catalyst system 110 at a temperature of from 200 degrees Celsius (° C.) to 600° C., from 200° C. to 550° C., from 200° C. to 500° C., from 200° C. to 450° C., from 200° C. to 400° C., from 200° C. to 350° C., from 300° C. to 600° C., from 300° C. to 550° C., from 300° C. to 500° C., from 300° C. to 450° C., from 300° C. to 400° C., from 300° C. to 350° C., from 350° C. to 600° C., from 350° C. to 550° C., from 350° C. to 500° C., from 350° C. to 450° C., from 350° C. to 400° C., from 400° C. to 600° C., from 400° C. to 550° C., from 400° C. to 500° C., or from 400° C. to 450° C. In one or more embodiments, the metathesis reaction and the cracking reaction are performed at a temperature of from 400° C. to 600° C. Furthermore, the inlet stream 118 containing butene may contact the multiple-stage catalyst system 110 at a pressure of from 1 bar to 30 bars, from 1 bar to 20 bars, from 1 bar to 10 bars, from 2 bars to 30 bars, from 2 bars to 20 bars, or from 2 bars to 10 bars. In one or more embodiments, the inlet stream 118 containing butene may contact the multiple-stage catalyst system 110 at atmospheric pressure.

Optionally, the metathesis catalyst 122, the cracking catalyst 124, or both may be pretreated prior to metathesis and cracking. For example, the multiple-stage catalyst system 110 having the metathesis catalyst 122 and cracking catalyst 124 loaded into the metathesis reaction zone 112 and the cracking reaction zone 114, respectively, may be pretreated with nitrogen gas ($N_2$) or other inert gas for a period from 1 hour to 5 hours before commencing the metathesis and cracking reactions. The pretreating temperature may be at least 400° C., or at least 500° C.

A process for producing propylene may comprise at least partially metathesizing butene in a metathesizing reaction zone 112 comprising a metathesis catalyst 122 to form a metathesis reaction product. As previously described in this disclose, the metathesis catalyst 122 may comprise a mesoporous silica-alumina catalyst support impregnated with metal oxide having a mesoporous silica-alumina catalyst support comprising from 5 weight percent to 50 weight percent alumina. The process may further comprise at least partially cracking the metathesis reaction product in a cracking reaction zone 114 comprising a cracking catalyst 124 to form a cracking reaction product. As previously described in this disclosure, the cracking catalyst 124 may comprise a MFI structured silica-containing catalyst, and the cracking reaction product may comprise propylene. In one or more embodiments, the metathesis reaction zone 112 and the cracking reaction zone 114 may be disposed within a reactor.

In one or more embodiments, the stream containing butene may include 1-butene and 2-butene. In some embodiments, the 2-butene in the stream containing butene may comprise cis-2-butene, trans-2-butene, or both. In one or more embodiments, the metathesis reaction product may include propylene and pentene. In some embodiments, the metathesis reaction product may further include one or more of unreacted 2-butene, unreacted 1-butene, and $C_5+$ olefins. In one or more embodiments, the cracking reaction product may include propylene. In one or more embodiments, at least a portion of the 2-butene isomerizes to 1-butene in the metathesis reaction zone 112.

The process for producing propylene may comprise introducing a stream comprising butene to the metathesis reaction zone 112 that includes the metathesis catalyst 122, at least partially metathesizing the stream comprising butene with the metathesis catalyst 122 to form a metathesis reaction product stream, passing the metathesis reaction product stream to a cracking reaction zone 114 that includes a cracking catalyst 124, and at least partially cracking the metathesis reaction product stream with the cracking catalyst 124 to form a cracking reaction product stream that includes propylene.

In one or more embodiments, the cracking reaction product stream produced by the multiple-stage catalyst system 110 may have at least an 80 mol. % conversion of butene and a propylene yield in mol. % of at least 30%. In some embodiments, the cracking reaction product stream may have at least an 85 mol. % conversion of butene and a propylene yield in mol. % of at least 40%. In some embodiments, the product stream may have at least a 10 mol. % yield of ethylene, or at least a 15 mol. % yield of ethylene, or at least a 20 mol. % yield of ethylene. In other embodiments, the product stream may have at least 45 mol. % yield of propylene, or at least a 50 mol. % yield of propylene. In one or more embodiments, the multi-stage catalyst system 110 and propylene processes of the present disclosure may produce propylene from butene without introducing externally added ethylene into the stream containing butene or into the reactor as a supplemental feed stream. In one or more embodiments, the multi-stage catalyst system 110 and propylene processes of the present disclosure may produce propylene from a butene containing stream that has less than 5 wt. % ethylene, or less than 1 wt. % ethylene.

Moreover, the cracking reaction product stream may include less than 1 wt. % aromatics. The cracking reaction product stream may also have less than 5 wt. % of alkanes and aromatics. Without being bound by theory, greater yields of aromatics and alkanes may indicate coke formation, which may result in catalyst deactivation.

EXAMPLES

The following examples show the preparation of various catalysts which are used in combination as in the presently disclosed multiple-stage catalyst systems.

Example 1: Preparation of Mesoporous Silica Catalyst Support Blanks

A mesoporous silica ($SiO_2$) catalyst support having no alumina ($Al_2O_3$) incorporated into the catalyst support was made and used as a comparison sample. In a typical preparation, the mesoporous silica catalyst support (100% $SiO_2$, 0% $Al_2O_3$) was first prepared by placing a quantity of a commercially available mesoporous silica, such as Q-10 from Fuji Sylysia (average pore diameter of 10 nm, average relative pore volume of 1.00 ml/g, and an average surface area of 300 $m^2$/g), in a ceramic plate and calcining the mesoporous silica at 200° C. for three hours and then at 575° C. for an additional 5 hours, with a ramping rate of 3° C. per minute to obtain a mesoporous silica catalyst support. The BET surface area, which was calculated using the Brunauer Emmett-Teller (BET) method described subsequently in this disclosure, and the pore volume of the mesoporous silica catalyst support, which has 100% $SiO_2$ and 0% $Al_2O_3$ are provided in Table 1, which is subsequently provided in this disclosure.

Example 2: Preparation of Mesoporous Silica-Alumina Catalyst Support Blanks

In a typical preparation, the mesoporous silica-alumina catalyst support ($SiO_2$—$Al_2O_3$ catalyst support) was first prepared by adding appropriate amounts of silica ($SiO_2$) and alumina ($Al_2O_3$), the combined amounts totaling 20 grams, to a beaker containing 50 milliliters (ml) of deionized (DI) water. The silica used was Q10 (silica) from Fuji Sylysia (average pore diameter of 10 nm, average relative pore volume of 1.00 ml/g, and an average surface area of 300 $m^2$/g), and the alumina used was aluminum oxide, gamma phase, catalyst support from Alfa Aesar. The relative amounts of silica and alumina added to the DI water were varied depending on the specific $SiO_2$—$Al_2O_3$ ratio intended. For example, in the case of 90 wt. % $SiO_2$ and 10 wt. % $Al_2O_3$, 18 grams (g) of silica and 2 grams of alumina were added to the 50 ml of DI water. Compositions of the $SiO_2$—$Al_2O_3$ catalyst supports were made having a weight ratio of silica to alumina of 90:10, 75:25, 50:50, 25:75, and 0:100.

For each composition, the silica-alumina solution in DI water was mixed for 2 hours using a magnetic stirrer operated at 580 rotations per minute (rpm). After mixing for 2 hours, each solution was placed in a rotary evaporator, which was rotated at 171 rpm and operated under a vacuum of 292 millibar (mbar) and at a temperature of 80° C. Cold water at a temperature of 6° C. was pumped into and through the rotary evaporator housing to enhance condensation. Each resulting composition was then placed in a drying oven overnight at 80° C. After drying, each of the $SiO_2$—$Al_2O_3$ catalyst support compositions were calcined at 200° C. for 3 hours and then at 575° C. for an additional 5 hours. The ramping rate from 200° C. to 575° C. was 3 degrees Celsius per minute (° C./min).

Figure 2:
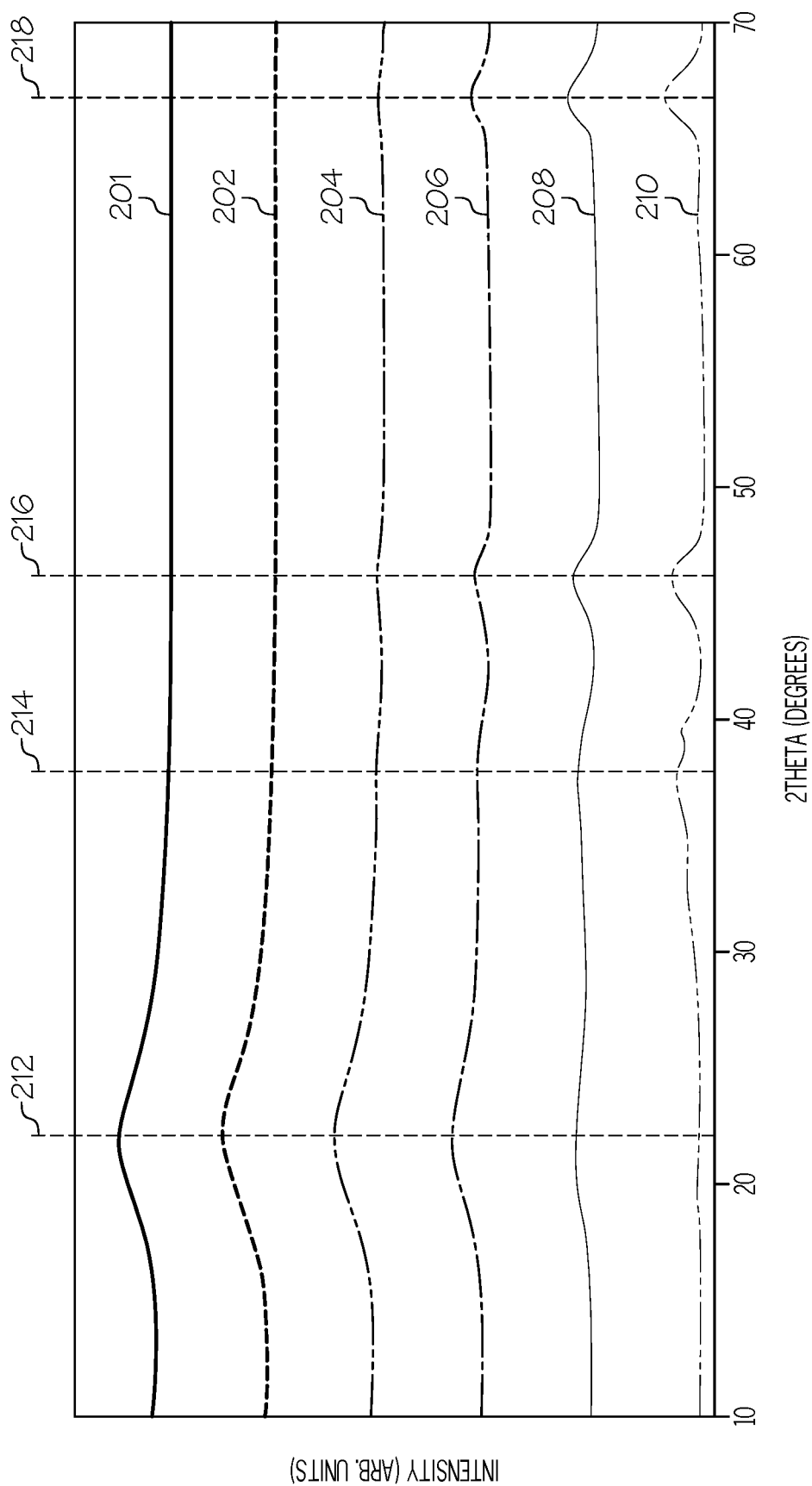
FIG. 2 is a X-Ray Diffraction (XRD) graph illustrating the XRD profiles of mesoporous silica-alumina catalyst supports, in accordance with one or more embodiments of the present disclosure.

The X-Ray Diffraction (XRD) patterns of each of the $SiO_2$—$Al_2O_3$ catalyst support compositions of Example 2, before impregnating the $SiO_2$—$Al_2O_3$ catalyst support compositions with tungsten oxide, are provided in FIG. 2. The $SiO_2$—$Al_2O_3$ catalyst support having 10 wt. % alumina is denoted by reference number 202; the $SiO_2$—$Al_2O_3$ catalyst support having 25 wt. % alumina is denoted by reference number 204; the $SiO_2$—$Al_2O_3$ catalyst support having 50 wt. % alumina is denoted by reference number 206; the $SiO_2$—$Al_2O_3$ catalyst support having 75 wt. % alumina is denoted by reference number 208; and the $SiO_2$—$Al_2O_3$ catalyst support having 100 wt. % alumina is denoted by reference number 210. FIG. 2 also provides the XRD pattern of the $SiO_2$ catalyst support of Example 1 having 0% alumina, which is denoted with reference number 201.

The XRD patterns of the $SiO_2$—$Al_2O_3$ catalyst supports having 0 wt. % alumina 201, 10 wt. % alumina 202, 25 wt. % alumina 204, 50 wt. % alumina 206, and 75 wt. % alumina 208 each show a broad peak generally centered on reference line 212 of FIG. 2 and extending between 2 theta (2θ)=20 degrees (°) and 2θ=25°. The broad peaks aligned with reference line 212 indicate the presence of silica in the composition. The XRD patterns of FIG. 2 show that the broad silica peak decreases in magnitude moving downward along line 212 from the $SiO_2$—$Al_2O_3$ catalyst support having 10 wt. % alumina 202 to the $SiO_2$—$Al_2O_3$ catalyst support having 100 wt. % alumina 210. This observation is consistent with the decreasing proportion of silica in the $SiO_2$—$Al_2O_3$ catalyst support compositions.

Further, the XRD patterns for the $SiO_2$—$Al_2O_3$ catalyst supports having 25 wt. % alumina 204, 50 wt. % alumina 206, 75 wt. % alumina 208, and 100 wt. % alumina 210 each show a peak at about 2θ=38° (aligned along reference line 214), a peak at about 2θ=47° (aligned along reference line 216), and a peak at about 2θ=67° (aligned along reference line 218), which may be attributed to the alumina present in the composition. The XRD patterns of FIG. 2 show that the alumina peaks at 2θ=38°, 2θ=47°, and 2θ=67° increase in magnitude moving from the $SiO_2$—$Al_2O_3$ catalyst support having 10 wt. % alumina 202 to the $SiO_2$—$Al_2O_3$ catalyst support having 100 wt. % alumina 210. This observation is consistent with the increasing proportion of silica in the $SiO_2$—$Al_2O_3$ catalyst support compositions. The relative magnitudes of the alumina peak and the silica peak for each of the $SiO_2$—$Al_2O_3$ compositions are in alignment with the relative ratio of silica and alumina in each composition.

Table 1 includes the mechanical properties of the mesoporous silica catalyst support of Example 1 and the mesoporous $SiO_2$—$Al_2O_3$ catalyst supports prepared in Example 2. As indicated in Table 1, the surface area and relative pore volume for the mesoporous $SiO_2$—$Al_2O_3$ catalyst supports generally decrease with increasing proportion of alumina.

TABLE 1

Surface Areas and Relative Pore Volumes of Silica and
Silica-Alumina Catalyst Supports of Examples 1 and 2

| Catalysts/Supports | BET Surface Area ($m^2/g$) | Relative Pore Volume ($cm^3/g$) |
|---|---|---|
| 100 wt. % $SiO_2$ + 0 wt. % $Al_2O_3$ | 304.41 | 1.13 |
| 90 wt. % $SiO_2$ + 10 wt. % $Al_2O_3$ | 305.45 | 0.94 |
| 75 wt. % $SiO_2$ + 25 wt. % $Al_2O_3$ | 282.37 | 1.00 |
| 50 wt. % $SiO_2$ + 50 wt. % $Al_2O_3$ | 253.46 | 0.95 |
| 25 wt. % $SiO_2$ + 75 wt. % $Al_2O_3$ | 231.98 | 0.79 |
| 0 wt. $SiO_2$ % + 100 wt. % $Al_2O_3$ | 204.82 | 0.70 |

Example 3: Preparation of the Metathesis Catalyst Supports Impregnated with Tungsten Oxide The mesoporous silica catalyst support of Example 1 and the mesoporous $SiO_2$—$Al_2O_3$ catalyst supports of Example 2, collectively referred to in this Example 3 as the catalyst support compositions, were impregnated with tungsten oxide ($WO_3$) to synthesize the metathesis catalysts. For each catalyst support composition, 2 grams of the catalyst support composition were placed in an 80 ml beaker. 0.235 grams of ammonium metatungstate hydrate [($NH_4$) $6H_2W_{12}O_{40}$·$xH_2O$] (99.99% trace metals basis) was mixed with 2 ml of DI water. The ammonium metatungstate hydrate solution was then added drop-wise to the 2 grams of catalyst support composition. Typically, 5 drops were placed on the catalyst support composition. A glass rod was used to thoroughly mix the catalyst support composition and the ammonium metatungstate hydrate solution. Subsequently, the catalyst support composition mixed with the ammonium metatungstate hydrate solution was placed in a drying oven overnight at 80° C. The dried catalyst support composition mixed with the ammonium metatungstate hydrate was calcined in a calcination oven at 250° C. for 2 hours, with a ramping rate of 1° C. per minute up to 250° C., and then calcined at 550° C. for 8 hours, with a ramping rate of 3° C. per min from 250° C. to 550° C. The resulting metathesis catalysts included the mesoporous $SiO_2$—$Al_2O_3$ catalyst supports impregnated with tungsten oxide ($WO_3$/$SiO_2$—$Al_2O_3$ catalyst), which were derived from the mesoporous $SiO_2$—$Al_2O_3$ catalyst supports of Example 2, and the mesoporous silica catalyst support impregnated with tungsten oxide, which was derived from the mesoporous $SiO_2$ catalyst support of Example 1 and as a comparative catalyst example. The process resulted in an amount of tungsten oxide of about 10 wt. % in the $WO_3$/$SiO_2$—$Al_2O_3$ catalysts and the $WO_3$/$SiO_2$ catalyst.

Figure 3:
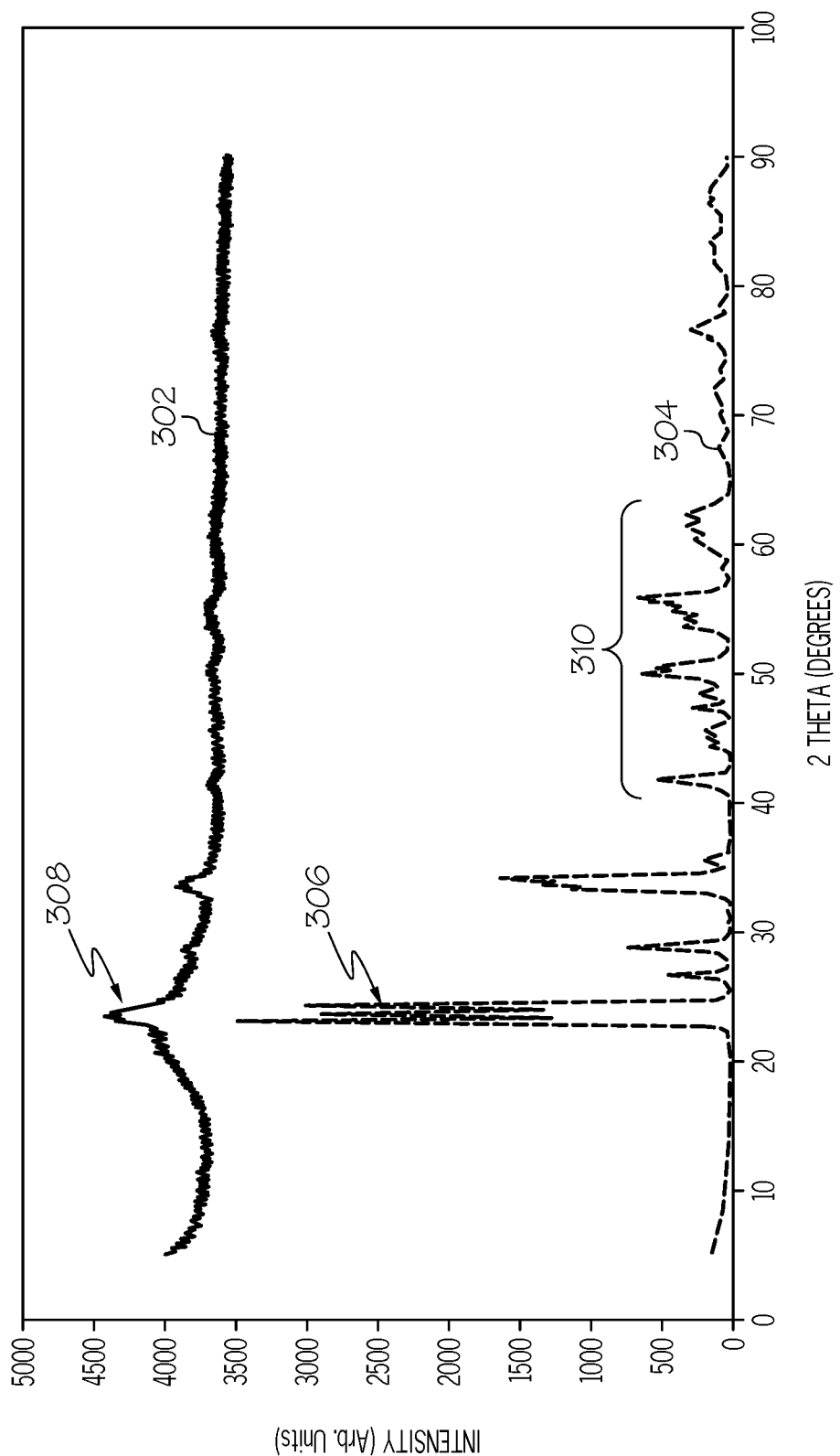
FIG. 3 is a XRD graph illustrating the XRD profile a mesoporous silica catalyst support and a mesoporous silica catalyst support impregnated with tungsten oxide.

The XRD pattern 304 of the $WO_3$/$SiO_2$ catalyst of Example 3, which was made from the mesoporous silica catalyst support of Example 1, is shown in FIG. 3. For comparison, FIG. 3 also includes the XRD pattern 302 for the mesoporous silica catalyst support of Example 1 without the tungsten oxide. The peak 306 of the XRD pattern for the $WO_3$/$SiO_2$ is aligned with the peak 308 of the mesoporous silica catalyst support without tungsten oxide, which indicates the presence of the silica in the mesoporous silica catalyst support. The plurality of peaks 310 in the XRD pattern between 2θ=40° and 2θ=65° indicate the presence of tungsten oxide in the $WO_3$/$SiO_2$ catalyst.

Table 2 includes the mechanical properties of the mesoporous silica catalyst support impregnated with tungsten oxide ($WO_3$/$SiO_2$ catalyst) and the mesoporous silica-alumina catalyst support impregnated with tungsten oxide having a weight ratio of silica to alumina of 75:25 ($WO_3$/($SiO_2$ 75%-$Al_2O_3$ 25%) catalyst), which were prepared in Example 3. As indicated in Table 2, the surface area, relative pore volume, and mean pore size for the $WO_3$/($SiO_2$ 75%-$Al_2O_3$ 25%) catalyst are generally less than the mesoporous silica catalyst support impregnated with tungsten oxide, which has no added alumina.

TABLE 2

Surface Areas, Relative Pore Volumes, and Mean Pore
Size Distributions of Metathesis Catalyst Supports
Impregnated with Tungsten Oxide of Example 3

| Catalysts Supports Impregnated with Tungsten Oxide | BET Surface Area ($m^2/g$) | Relative Pore Volume ($cm^3/g$) | Mean Pore Size Distribution (Å) |
|---|---|---|---|
| $WO_3$/$SiO_2$ 100% | 279 | 1.22 | 175 |
| $WO_3$/($SiO_2$ 75%-$Al_2O_3$ 25%) | 283 | 0.9934 | 142 |

Example 4: Preparation of Silicalite-1 Cracking Catalyst

In a typical synthesis, 4.26 grams tetrapropylammonium bromide (TPABr) and 0.7407 grams ammonium fluoride ($NH_4F$) were dissolved in 72 ml of DI water and stirred well for 15 minutes. Then, 12 grams of fumed silica ($SiO_2$) were added and stirred well until homogenized. The resulting gel was autoclaved and kept at 200° C. for 2 days. The molar composition of the gel was 1 $SiO_2$: 0.08 TPABr: 0.10 $NH_4F$: 20 $H_2O$. The solid products obtained were washed with water and dried at 80° C. overnight. The template was removed by calcination in air at 750° C. for 5 hours at a ramping rate of 3° C. per min.

Example 5: Preparation of MFI-2000 Cracking Catalyst

In a typical synthesis, 8.52 grams of TPABr and 1.48 grams of $NH_4F$ were dissolved in 150 ml of DI water, and the resulting TPABr solution was stirred well for 20 minutes. Then, 24 grams fumed silica and 0.15 grams of aluminum nitrate were gradually added simultaneously to the TPABr solution while stirring vigorously. Once the solution gelled, the gel was mixed vigorously with a spatula for approximately 10 minutes until homogenized. The obtained gel was autoclaved and kept at 200° C. for 2 days. After two days the autoclave was removed from the oven and quenched in cold water for 30 minutes. The molar composition of the gel was 1 $SiO_2$: 0.0005 $Al_2O_3$: 0.08 (TPA)Br: 0.10 $NH_4F$: 20 $H_2O$. The solid products obtained were removed from the autoclave, filtered, washed with 1 liter of DI water, and dried at 80° C. overnight. The solid products were removed from the drying oven and calcined at 750° C. for 6 hours with a ramp up of 4° C. per min, producing the MFI-2000 cracking catalyst.

Catalyst Evaluation

The prepared catalysts from Examples 1-5 were tested in a dual-stage catalyst system to evaluate their activity and selectivity for converting 2-butene to propylene in a fixed-bed continuous flow reactor (ID 0.25 inches (in), Autoclave Engineers Ltd.) at atmospheric pressure. For each run, fixed amounts of each catalyst—the metathesis catalyst (one of the mesoporous $SiO_2$ or $SiO_2$—$Al_2O_3$ catalyst supports impregnated with tungsten oxide of Examples 1-3) and the cracking catalyst (MFI-2000 from Example 5)—were packed into the reactor tube with grade 20 silicon carbide at the bottom of the reactor to form the dual-stage catalyst system. The grade 20 silicon carbide is chemically inert and makes no contribution to the reaction chemistry. The metathesis catalyst and cracking catalyst were separated from each other by quartz wool. Additional layers of quartz wool were placed between the catalyst and the silicon carbide and at the inlet and outlet ends of the reactor.

The temperature of the reactor was ramped up from room temperature to a temperature of 550° C. over a period of 90 minutes with $N_2$ at a flow rate of 50 standard cubic centimeters per minute (sscm). Once the reactor reached 550° C., the catalysts were pretreated and activated under $N_2$ at 550° C. and a flow of 25 sccm for 60 minutes (min). All reactions were carried out at three temperatures: 450° C., 500° C., and 550° C. All reactions were carried out at atmospheric pressure at a gas hourly space velocity (GHSV) of 900 $h^{-1}$ and using a feed stream that included 2-butene (5 milliliters/minute (ml/min)) with nitrogen as diluent (25 ml/min). For each reaction at each reaction temperature, the reactor was maintained at the reaction temperature for 3.5 hours.

Example 6: Comparative Example of the Dual-Stage Catalyst System with the Mesoporous Silica Catalyst Support Impregnated with Tungsten Oxide Comparative examples of a dual-stage catalyst system utilizing the mesoporous silica catalyst support impregnated with tungsten oxide ($WO_3/SiO_2$) as the metathesis catalyst were conducted and the product stream tested for yield, conversion, and selectivity for converting 2-butene to propylene. The comparative example reactions were conducted in the fixed-bed continuous flow reactor (ID 0.25 in, Autoclave Engineers Ltd.) at atmospheric pressure. The dual catalyst system was prepared having a layer of the $WO_3/SiO_2$ metathesis catalyst (1 ml) and a layer of the cracking catalyst of Example 5 (1 ml) positioned downstream of the $WO_3/SiO_2$ metathesis catalyst. The total catalyst load was 2 ml.

A layer of silicon carbide was positioned in the bottom of the reactor, downstream of the cracking catalyst. Quartz wool was positioned upstream of the layer of $WO_3/SiO_2$ metathesis catalyst, between the layer of $WO_3/SiO_2$ catalyst and the layer of cracking catalyst, between the layer of cracking catalyst and the silicon carbide, and downstream of the silicon carbide. The dual-stage catalyst reactor system having $WO_3/SiO_2$ for the metathesis catalyst was run at three reaction temperatures, 450° C., 500° C., and 550° C.

The temperature of the reactor was ramped up from room temperature to a temperature of 550° C. over a period of 90 minutes with $N_2$ at a flow rate of 50 standard cubic centimeters per minute (sscm). Once the reactor reached 550° C., the catalysts of the dual-stage catalyst system of Example 6 were pretreated and activated under $N_2$ at 550° C. and a flow of 25 sccm for 60 min. All reactions were carried out at atmospheric pressure at a GHSV of 900 $h^{-1}$ and using a feed stream that included 2-butene (5 ml/min) with nitrogen as diluent (25 ml/min). For each reaction temperature, the reactor was maintained at the reaction temperature for 3.5 hours. Quantitative analysis of the reaction products for each experiment was performed using an Agilent gas chromatograph with flame ionization detector (FID) (Agilent GC-7890B), equipped with an HP—Al/KCL (50 m×0.53 mm×15 microns) column.

Table 3 summarizes the yields, conversions and selectivity obtained for the dual-stage catalyst system having $WO_3/SiO_2$ as the metathesis catalyst of comparative Example 6. In Table 3, the values of the yields and conversions of the 2-butene feed were calculated based on an average of values obtained from 5 injections into the gas chromatograph at each temperature once the reaction run was stable.

TABLE 3

Performance of the Dual Stage Catalyst System Having $WO_3/SiO_2$ as the Metathesis Catalyst of Comparative Example 6
Comparative Example 6: $WO_3/SiO_2$ - MFI 2000 Dual-Stage Catalyst System

| | Temperature (° C.) | | |
|---|---|---|---|
| Yields | 450 | 500 | 550 |
| Methane (mol %) | 0.000 | 0.101 | 0.238 |
| Ethane (mol %) | 0.074 | 0.102 | 0.151 |
| Ethylene (mol %) | 7.107 | 10.391 | 14.489 |
| Propane (mol %) | 2.801 | 2.232 | 1.727 |
| Propylene (mol %) | 33.409 | 38.897 | 43.360 |
| Iso-butane (mol %) | 4.101 | 2.324 | 1.131 |
| N-butane (mol %) | 2.430 | 1.710 | 1.039 |
| Trans-butene (mol %) | 7.670 | 7.340 | 7.073 |
| 1-Butene (mol %) | 4.117 | 4.402 | 4.579 |
| Isobutene (mol %) | 13.220 | 12.013 | 10.960 |
| Cis-butene (mol %) | 5.371 | 5.250 | 5.119 |
| C5 (mol %) | 13.100 | 10.132 | 6.718 |
| C6+ (mol %) | 6.637 | 5.126 | 3.418 |
| Total Olefins (mol %) | 40.516 | 49.288 | 57.849 |
| Conversion (%) | 86.959 | 87.410 | 87.808 |
| Conversion-C4 (%) | 69.622 | 70.994 | 72.270 |
| Propylene Selectivity | 38.420 | 44.501 | 49.379 |
| Ethylene Selectivity | 8.172 | 11.888 | 16.499 |
| Isobutene Selectivity | 15.203 | 13.744 | 12.481 |

As shown in Table 3, increasing the reaction temperature increased the propylene yield. The maximum propylene yield of 43.360 mol % was attained at 550° C. Increasing the reaction temperature also increased the ethylene yield, overall conversion, propylene selectivity, and ethylene selectivity. The yield and selectivity for isobutene, an unwanted byproduct of the reaction system, decreased with increasing temperature.

Figure 4:
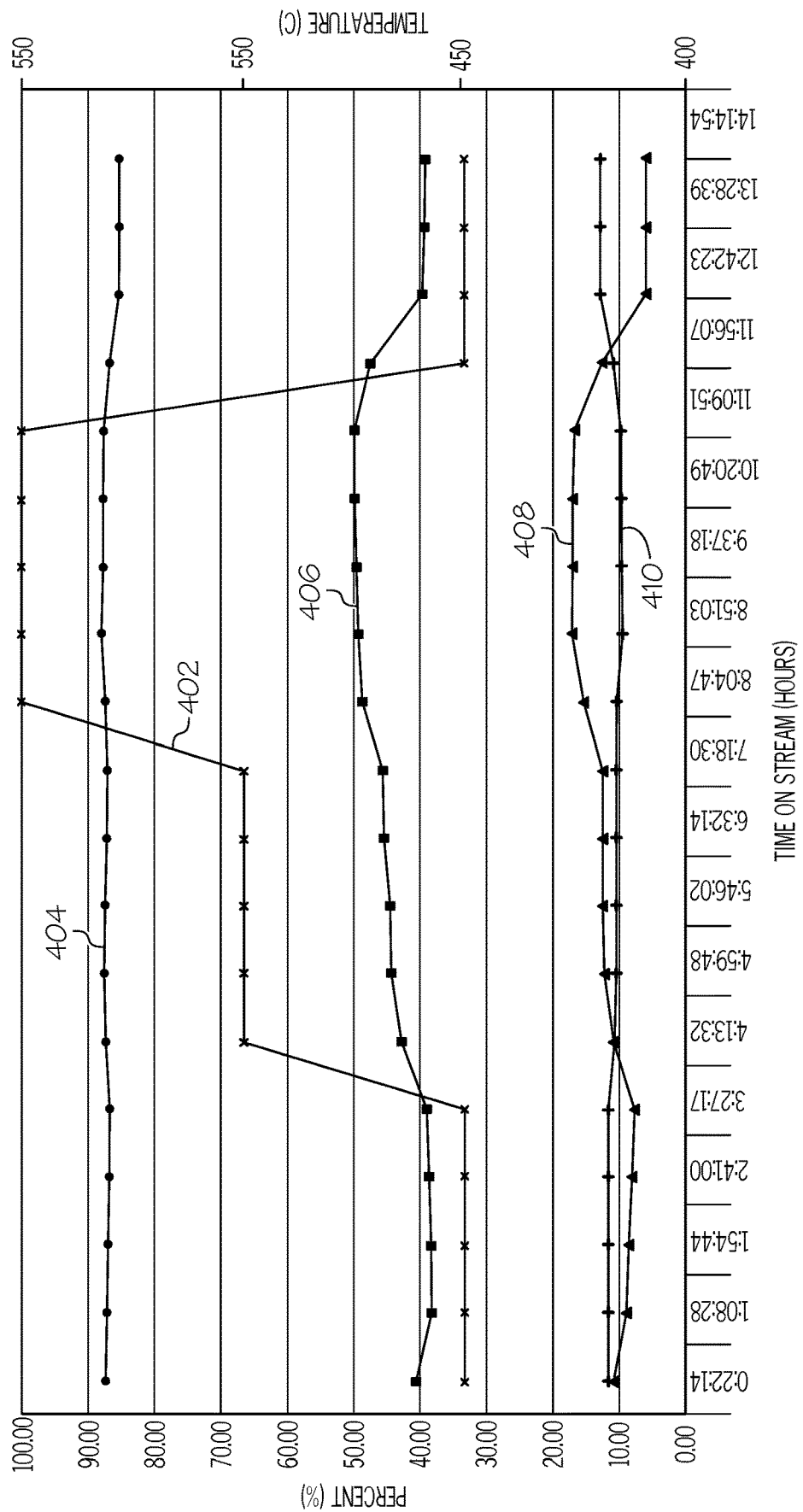
FIG. 4 is a graph illustrating the performance of a dual-stage catalyst system over time and reaction temperature changes, in accordance with one or more embodiments of the present disclosure.

With reference to FIG. 4, the dual-stage catalyst system having the $WO_3/SiO_2$ metathesis catalyst demonstrates a stable conversion and selectivity at various temperatures over a period of time. The dual-stage catalyst system of Example 6 was utilized for the reaction of 2-butene to propylene at reaction temperatures of 450° C., 500° C., and 550° C. at atmospheric pressure with a GHSV of 900 $h^{-1}$. The data of FIG. 4 is also subsequently presented in Table 4. FIG. 4 illustrates the reaction temperature 402, overall conversion 404, selectivity of propylene 406, selectivity of ethylene 408, and selectivity of isobutene 410 as a function of time on stream for the dual-stage catalyst system of Example 6. The slope of the overall conversion 404, selectivity of propylene 406, and selectivity of ethylene 408 are all steady or increasing throughout the 14+ hour run time of the reaction system represented in FIG. 4, which indicates that the dual-catalyst system may be stable and no deactivation of the downstream catalyst may have occurred.

TABLE 4

Temperature, Conversion, and Selectivity versus On-Stream Time for the Dual-Stage Catalyst System of Comparative Example 6 Having a WO$_3$/SiO$_2$ Metathesis Catalyst
Example 6: Temperature, Conversion, and Selectivity Versus Time On Stream

| On Stream Time (hr:min:sec) | Temperature (° C.) | Overall Conversion (mol %) | Propylene Selectivity (%) | Ethylene Selectivity (%) | Isobutene Selectivity (%) |
|---|---|---|---|---|---|
| 0:22:14 | 450 | 87.55 | 40.42 | 10.69 | 11.38 |
| 1:08:28 | 450 | 87.22 | 38.14 | 8.84 | 11.33 |
| 1:54:44 | 450 | 87.01 | 38.22 | 8.21 | 11.45 |
| 2:41:00 | 450 | 86.83 | 38.52 | 7.92 | 11.57 |
| 3:27:17 | 450 | 86.77 | 38.81 | 7.72 | 11.64 |
| 4:13:32 | 500 | 87.47 | 42.72 | 10.73 | 10.65 |
| 4:59:48 | 500 | 87.66 | 44.40 | 12.05 | 10.28 |
| 5:46:02 | 500 | 87.58 | 44.54 | 12.28 | 10.34 |
| 6:32:14 | 500 | 87.22 | 45.33 | 12.26 | 10.55 |
| 7:18:30 | 500 | 87.12 | 45.52 | 12.11 | 10.57 |
| 8:04:47 | 550 | 87.51 | 48.54 | 15.17 | 10.06 |
| 8:51:03 | 550 | 88.18 | 49.31 | 17.07 | 9.37 |
| 9:37:18 | 550 | 87.83 | 49.38 | 16.79 | 9.58 |
| 10:23:35 | 550 | 87.84 | 49.84 | 16.85 | 9.51 |
| 11:09:51 | 550 | 87.69 | 49.83 | 16.61 | 9.60 |
| 11:56:07 | 450 | 86.67 | 47.45 | 12.53 | 10.88 |
| 12:42:23 | 450 | 85.51 | 39.69 | 6.16 | 12.51 |
| 13:28:39 | 450 | 85.49 | 39.24 | 5.92 | 12.49 |
| 14:14:54 | 450 | 85.41 | 39.18 | 5.83 | 12.62 |

Example 7: Dual-Stage Catalyst System with a Mesoporous Silica-Alumina Catalyst Support Impregnated with Tungsten Oxide Metathesis Catalyst Examples of a dual-stage catalyst system utilizing the mesoporous silica-alumina catalyst support impregnated with tungsten oxide as the metathesis catalyst were conducted and the product stream tested for yield, conversion, and selectivity for converting 2-butene to propylene. The mesoporous silica-alumina catalyst support impregnated with tungsten oxide from Example 6 having a weight ratio of silica to alumina in the catalyst support of 75:25 (WO$_3$/(SiO$_2$ 75%-Al$_2$O$_3$ 25%) catalyst) was used. The reactions of Example 7 were conducted in the fixed-bed continuous flow reactor (ID 0.25 in, Autoclave Engineers Ltd.) at atmospheric pressure. The dual-stage catalyst system was prepared having a layer of the WO$_3$/(SiO$_2$ 75%-Al$_2$O$_3$ 25%) metathesis catalyst (1 ml) and a layer of the cracking catalyst of Example 5 (1 ml) positioned downstream of the WO$_3$/(SiO$_2$ 75%-Al$_2$O$_3$ 25%) metathesis catalyst. The total catalyst load was 2 ml.

A layer of silicon carbide was positioned in the bottom of the reactor, downstream of the cracking catalyst. Quartz wool was positioned upstream of the layer of WO$_3$/(SiO$_2$ 75%-Al$_2$O$_3$ 25%) metathesis catalyst, between the layer of WO$_3$/(SiO$_2$ 75%-Al$_2$O$_3$ 25%) catalyst and the layer of cracking catalyst, between the layer of cracking catalyst and the silicon carbide, and downstream of the silicon carbide. The dual-stage catalyst reactor system having WO$_3$/(SiO$_2$ 75%-Al$_2$O$_3$ 25%) catalyst for the metathesis catalyst was run at three reaction temperatures, 450° C., 500° C., and 550° C.

The temperature of the reactor was ramped up from room temperature to a temperature of 550° C. over a period of 90 minutes with N$_2$ at a flow rate of 50 standard cubic centimeters per minute (sscm). Once the reactor reached 550° C., the catalysts of the dual-stage catalyst system of Example 7 were pretreated and activated under N$_2$ at 550° C. and a flow of 25 sccm for 60 min. All reactions were carried out at atmospheric pressure at a GHSV of 900 h$^{-1}$ and using a feed stream that included 2-butene (5 ml/min) with nitrogen as diluent (25 ml/min). For each reaction temperature, the reactor was maintained at the reaction temperature for 3.5 hours. Quantitative analysis of the reaction products at each reaction temperature was performed using the Agilent gas chromatograph previously described in Example 6.

Table 5 summarizes the yields, conversions and selectivity obtained for the dual-stage catalyst system of Example 7 having the WO$_3$/(SiO$_2$ 75%-Al$_2$O$_3$ 25%) catalyst as the metathesis catalyst of Example 7. In Table 5, the values of the yields and conversions of the 2-butene feed were calculated based on an average of values obtained from 5 injections into the gas chromatograph at each temperature once the reaction run was stable.

TABLE 5

Performance of Dual Stage Catalyst System Having WO$_3$/(SiO$_2$ 75%-Al$_2$O$_3$ 25%) as the Metathesis Catalyst
Example 7: WO$_3$/(SiO$_2$ 75%-Al$_2$O$_3$ 25%) - MFI 2000 Dual-Stage Catalyst System

| Yields | Temperature (° C.) | | |
|---|---|---|---|
| | 450 | 500 | 550 |
| Methane (mol %) | 0.098 | 0.189 | 0.426 |
| Ethane (mol %) | 0.089 | 0.140 | 0.227 |
| Ethylene (mol %) | 8.272 | 11.295 | 15.045 |
| Propane (mol %) | 2.943 | 2.058 | 1.571 |
| Propylene (mol %) | 34.365 | 39.867 | 44.289 |
| Iso-butane (mol %) | 4.014 | 1.880 | 0.993 |
| N-butane (mol %) | 2.223 | 1.465 | 1.071 |
| Trans-butene (mol %) | 7.206 | 6.967 | 6.840 |
| 1-Butene (mol %) | 4.613 | 5.018 | 5.467 |
| Isobutene (mol %) | 13.199 | 12.045 | 11.364 |
| Cis-butene (mol %) | 5.228 | 5.138 | 5.179 |
| C5 (mol %) | 12.009 | 9.493 | 6.501 |
| C6+ (mol %) | 5.819 | 4.445 | 1.025 |
| Total Olefins (mol %) | 42.638 | 51.162 | 59.334 |
| Conversion (%) | 87.567 | 87.896 | 87.981 |
| Conversion-C4 (%) | 69.755 | 70.833 | 71.150 |
| Propylene Selectivity | 39.242 | 45.357 | 50.341 |
| Ethylene Selectivity | 9.444 | 12.851 | 17.101 |
| Isobutene Selectivity | 15.073 | 13.704 | 12.916 |

As shown in Table 5, increasing the reaction temperature increased the propylene yield. The maximum propylene yield of 44.289 mol % was attained at 550° C. Increasing the reaction temperature also increased the ethylene yield, overall conversion, propylene selectivity, and ethylene selectivity. The yield and selectivity for isobutene, an unwanted byproduct of the reaction system, decreased with increasing temperature. Table 6, provided subsequently, compares the performance of the dual-stage catalyst system of Example 7 having the WO$_3$/(SiO$_2$ 75%-Al$_2$O$_3$ 25%) catalyst as the metathesis catalyst with the dual-stage catalyst system of Example 6 having the WO$_3$/SiO$_2$ as the metathesis catalyst at each reaction temperature. Table 6 further provides an indication of the change in performance between the WO$_3$/SiO$_2$ catalyst and the WO$_3$/(SiO$_2$ 75%-Al$_2$O$_3$ 25%) catalyst as the metathesis catalyst. An improvement for each measured property was calculated by dividing the difference between Example 7 and Example 6 by Example 6 and multiplying the quotient by 100 to convert the improvement to a percent (%). A negative change in the isobutene selectivity is reported as a positive improvement since isobutene is an unwanted byproduct.

TABLE 6

Comparison of the Propylene Yield, Ethylene Yield, Overall Conversion, and Selectivity of Examples 6 and 7

| | Example 6 | Example 7 | Change | Improvement (%) |
|---|---|---|---|---|
| Metathesis Catalyst | $WO_3/SiO_2$ | $WO_3/$ $(SiO_2\ 75\%\text{-}Al_2O_3\ 25\%)$ | n/a | n/a |
| Temperature = 450° C. | | | | |
| Propylene Yield (mol %) | 33.409 | 34.365 | 0.956 | 2.9% |
| Ethylene Yield (mol %) | 7.107 | 8.272 | 1.165 | 16.4% |
| Overall Conversion (%) | 86.959 | 87.567 | 0.608 | 0.7% |
| Propylene Selectivity | 38.420 | 39.242 | 0.822 | 2.1% |
| Ethylene Selectivity | 8.172 | 9.444 | 1.272 | 15.6% |
| Isobutene Selectivity | 15.203 | 15.073 | −0.130 | 10.8% |
| Temperature = 500° C. | | | | |
| Propylene Yield (mol %) | 38.897 | 39.867 | 0.970 | 2.5% |
| Ethylene Yield (mol %) | 10.391 | 11.295 | 0.904 | 8.7% |
| Overall Conversion (%) | 87.410 | 87.896 | 0.486 | 0.6% |
| Propylene Selectivity | 44.501 | 45.357 | 0.856 | 1.9% |
| Ethylene Selectivity | 11.888 | 12.851 | 0.963 | 8.1% |
| Isobutene Selectivity | 13.744 | 13.704 | −0.040 | 0.3% |
| Temperature = 550° C. | | | | |
| Propylene Yield (mol %) | 43.360 | 44.289 | 0.929 | 2.1% |
| Ethylene Yield (mol %) | 14.489 | 15.045 | 0.556 | 3.8% |
| Overall Conversion (%) | 87.808 | 87.981 | 0.173 | 0.2% |
| Propylene Selectivity | 49.379 | 50.341 | 0.962 | 2.0% |
| Ethylene Selectivity | 16.499 | 17.101 | 0.602 | 3.7% |
| Isobutene Selectivity | 12.481 | 12.916 | 0.435 | −3.5% |

As shown in Table 6, utilization of the $WO_3/(SiO_2\ 75\%\text{-}Al_2O_3\ 25\%)$ metathesis catalyst in the dual-stage catalyst system of Example 7 resulted in increases in propylene yield of 2.9% at 450° C., 2.5% at 500° C., and 2.1% at 550° C. The yield of ethylene, overall conversion, propylene selectivity, and ethylene selectivity of the dual-stage catalyst system with the $WO_3/(SiO_2\ 75\%\text{-}Al_2O_3\ 25\%)$ metathesis catalyst was improved at each temperature over the dual-stage catalyst system of Example 6 having the $WO_3/SiO_2$ metathesis catalyst. Utilization of the $WO_3/(SiO_2\ 75\%\text{-}Al_2O_3\ 25\%)$ metathesis catalyst resulted in a reduction in the selectivity of isobutene at reaction temperatures of 450° C. and 500° C.

Figure 5:
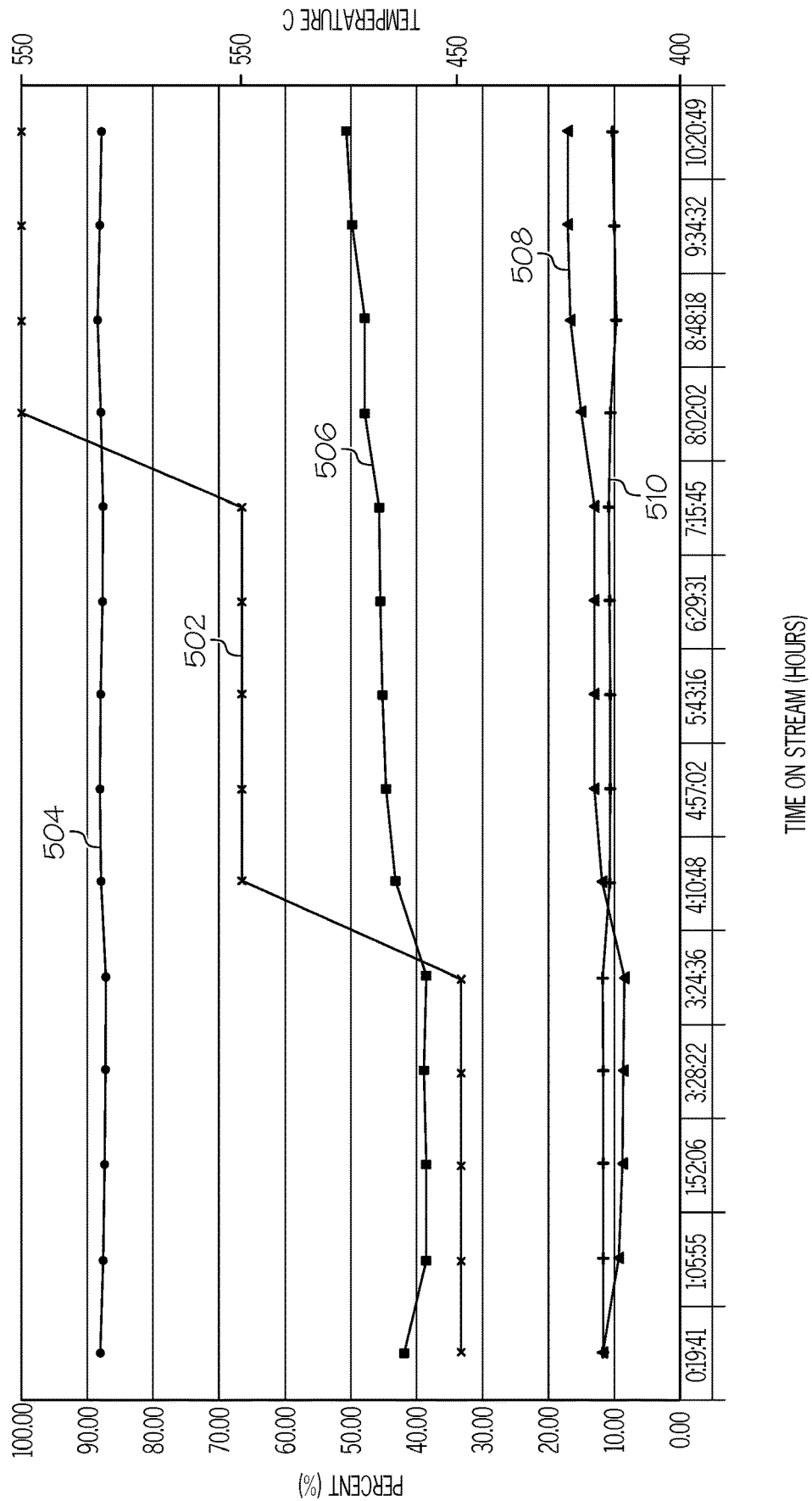
FIG. 5 is a graph illustrating the performance of a dual-stage catalyst system over time and reaction temperature changes, in accordance with one or more embodiments of the present disclosure.

With reference to FIG. 5, the dual-stage catalyst system having the $WO_3/(SiO_2\ 75\%\text{-}Al_2O_3\ 25\%)$ metathesis catalyst demonstrates a stable conversion and selectivity at various temperatures over a period of time. The dual-stage catalyst system of Example 7 was utilized for the reaction of 2-butene to propylene at reaction temperatures of 450° C., 500° C., and 550° C. and at atmospheric pressure with a GHSV of 900 $h^{-1}$. The data of FIG. 5 is also subsequently presented in Table 7. FIG. 5 illustrates the reaction temperature 502 (° C.), overall conversion 504 (%), selectivity of propylene 506, selectivity of ethylene 508, and selectivity of isobutene 510 as a function of time on stream for the dual-stage catalyst system of Example 7. The slope of the overall conversion 504, selectivity of propylene 506, and selectivity of ethylene 508 are all steady or increasing throughout the 10+ hour run time of the reaction system represented in FIG. 5, which indicates that the dual-catalyst system having the $WO_3/(SiO_2\ 75\%\text{-}Al_2O_3\ 25\%)$ metathesis catalyst in the upstream reaction zone may be stable and no deactivation of the downstream catalyst may have occurred.

TABLE 7

Temperature, Conversion, and Selectivity versus On-Stream Time for the Dual-Stage Catalyst System of Example 7 Having a $WO_3/(SiO_2\ 75\%\text{-}Al_2O_3\ 25\%)$ Metathesis Catalyst
Example 7: Temperature, Conversion, and Selectivity Versus Time On Stream

| On Stream Time (hr:min:sec) | Temperature (° C.) | Overall Conversion (mol %) | Propylene Selectivity (%) | Ethylene Selectivity (%) | Isobutene Selectivity (%) |
|---|---|---|---|---|---|
| 0:19:41 | 450 | 87.97 | 41.77 | 11.76 | 11.48 |
| 1:05:55 | 450 | 87.69 | 38.53 | 9.47 | 11.41 |
| 1:52:06 | 450 | 87.55 | 38.45 | 8.98 | 11.52 |
| 2:38:22 | 450 | 87.36 | 38.85 | 8.64 | 11.66 |
| 3:24:36 | 450 | 87.26 | 38.62 | 8.37 | 11.71 |
| 4:10:48 | 500 | 87.94 | 43.19 | 11.71 | 10.72 |
| 4:57:02 | 500 | 88.05 | 44.87 | 13.03 | 10.50 |
| 5:43:16 | 500 | 87.98 | 45.27 | 12.94 | 10.48 |
| 6:29:31 | 500 | 87.85 | 45.51 | 12.80 | 10.61 |
| 7:15:45 | 500 | 87.70 | 45.79 | 12.63 | 10.76 |
| 8:02:02 | 550 | 87.91 | 48.00 | 15.14 | 10.29 |
| 8:48:18 | 550 | 88.56 | 47.92 | 16.72 | 9.59 |
| 9:34:32 | 550 | 88.16 | 49.84 | 17.02 | 9.84 |
| 10:20:49 | 550 | 87.80 | 50.84 | 17.18 | 10.15 |

As demonstrated by the results previously discussed for Examples 1-7, utilizing a mesoporous silica-alumina catalyst support impregnated with metal oxide as the metathesis catalyst in a multiple-stage catalyst system for producing propylene from butene showed an unexpected increase in the yield of propylene, yield of ethylene, overall conversion, and propylene selectivity over a multiple-stage catalyst system utilizing a mesoporous silica catalyst support impregnated with metal oxide and without any alumina. Without being bound by theory, the presence of alumina in the metathesis catalyst may increase isomerization of 2-butene in the butene containing inlet stream to 1-butene as compared to a metathesis catalyst containing only silica. Increasing the isomerization of 2-butene to 1-butene may increase the availability of 1-butene so that sufficient quantities of both 2-butene and 1-butene are available to undergo further conversion to propylene and other alkenes through cross-metathesis by the mesoporous silica-alumina catalyst support impregnated with metal oxide. This may result in increased concentration of propylene, ethylene, and other $C_5+$ alkenes in the metathesis reaction product and overall increased yield, conversion, and propylene selectivity of the multiple-stage catalyst system.

Moreover, the results previously discussed for Examples 1-7 indicate that utilization of the mesoporous silica-alumina catalyst support impregnated with metal oxide as the metathesis catalyst in a multiple-stage catalyst system results in an improvement in performance over a multiple-stage catalyst system having a mesoporous silica metathesis catalyst over a broad range of reaction temperatures. By using a combination metathesis catalyst that includes both silica and alumina in the mesoporous catalyst support, the metathesis reaction of butene to propylene may be conducted at a lesser operating temperature while producing the same or greater yields of propylene and ethylene and decreasing unwanted side reactions that produce undesired products as compared to a multiple-stage catalyst system having a silica-based metathesis catalyst with no alumina. A lesser operating temperature may also result in a decrease in energy costs to provide additional heating, which may reduce the operating costs of the multiple-stage catalyst system, among other benefits.

Calculation Methodologies

Determination of "Conversion" was calculated according to formula 1, where $n_i$ is the number of moles of component "i" (2-butenes) entering or leaving the reactor.

$$\text{Conversion} = \frac{n_{i,in} - n_{i,out}}{n_{i,in}} \times 100 \quad (1)$$

Similarly, determination of "Conversion-$C_4$" was calculated according to formula 2.

$$\text{Conversion} - C4 = 100 - (\text{CisButene Yield} + \text{TransButene Yield} + \text{IsoButene Yield} + 1-\text{Butene Yield}) \quad (2)$$

Determination of "Selectivity" was calculated according to formula 3.

$$\text{Selectivity} = \frac{\text{Yield of Product}}{\text{Conversion}} \times 100 \quad (3)$$

The surface area of the samples was measured by nitrogen adsorption at 77 Kelvin (K) using AUTOSORB-1 (Quanta Chrome). Before adsorption measurements, samples (ca. 0.1 g) were heated at 220° C. for 2 hours under nitrogen ($N_2$) flow. The $N_2$ adsorption isotherms of the catalysts were measured at a liquid nitrogen temperature of 77 Kelvin (K). The surface areas were calculated by the Brunauer Emmett-Teller (BET) method. The total relative pore volume was estimated from the amount of $N_2$ adsorbed at $P/P_0=0.99$. Barret E P, Joyner L J, Halenda P H, J. Am. Chem. Soc. 73 (1951) 373-380.

A first aspect of the present disclosure may be directed to a process for producing propylene, the process comprising at least partially metathesizing butene in a metathesizing reaction zone comprising a metathesis catalyst to form a metathesis reaction product, the metathesis catalyst comprising a mesoporous silica-alumina catalyst support impregnated with metal oxide having a mesoporous silica-alumina catalyst support comprising from 5 weight percent to 50 weight percent alumina. The process may further include at least partially cracking the metathesis reaction product in a cracking reaction zone comprising a cracking catalyst to form a cracking reaction product, where the cracking catalyst comprises a MFI structured silica-containing catalyst and the cracking reaction product comprises propylene.

A second aspect of the present disclosure may include the first aspect further comprising introducing a feed stream comprising the butene to the metathesizing reaction zone.

A third aspect of the present disclosure may include the second aspect where the feed stream is a raffinate-2 stream from a fluidized catalytic cracking (FCC) reactor or an ethylene cracking reactor.

A fourth aspect of the present disclosure may include either of the second and third aspects, where the feed stream comprises from 20 wt. % to 60 wt. % of cis- or trans-2-butene, or both, from 10 wt. % to 20 wt. % of 1-butene, and from 5 wt. % to 20 wt. % n-butane.

A fifth aspect of the present disclosure may include any of the first through fourth aspects where the mesoporous silica-alumina catalyst support of the mesoporous silica-alumina catalyst support impregnated with metal oxide comprises from 10 weight percent to 40 weight percent alumina.

A sixth aspect of the present disclosure may include any of the first through fifth aspects where the metal oxide of the combination catalyst support impregnated with metal oxide comprises one or more oxides of molybdenum, rhenium, tungsten, or combinations of these oxides.

A seventh aspect of the present disclosure may include any of the first through sixth aspects where the metal oxide of the mesoporous silica-alumina catalyst support impregnated with metal oxide comprises tungsten oxide.

An eighth aspect of the present disclosure may include any of the first through seventh aspects where the mesoporous silica-alumina catalyst support impregnated with metal oxide comprises from 1 weight percent to 30 weight percent tungsten oxide.

A ninth aspect of the present disclosure may include any of the first through eighth aspects where the mesoporous silica-alumina catalyst support impregnated with metal oxide comprises from 5 weight percent to 20 weight percent tungsten oxide.

A tenth aspect of the present disclosure may include any of the first through ninth aspects where the mesoporous silica-alumina catalyst support impregnated with metal oxide includes a pore size distribution from 2.5 nm to 40 nm.

An eleventh aspect of the present disclosure may include any of the first through tenth aspects where the mesoporous silica-alumina catalyst support impregnated with metal oxide comprises a total pore volume of at least 0.600 cm$^3$/g.

A twelfth aspect of the present disclosure may include any of the first through eleventh aspects where the MFI structured silica-containing catalyst comprises alumina.

A thirteenth aspect of the present disclosure may include any of the first through twelfth aspects where the MFI structured silica-containing catalyst comprises less than 0.01 wt. % alumina.

A fourteenth aspect of the present disclosure may include any of the first through thirteenth aspects where the MFI structured silica-containing catalyst comprises a total acidity from 0.001 mmol/g to 0.1 mmol/g.

A fifteenth aspect of the present disclosure may include any of the first through fourteenth aspects where the cracking reaction zone is downstream of the metathesis reaction zone.

A sixteenth aspect of the present disclosure may include any of the first through fifteenth aspects where the metathesis reaction zone and the cracking reaction zone are disposed within a single reactor.

A seventeenth aspect of the present disclosure may include any of the first through sixteenth aspects where the butene comprises 2-butene.

An eighteenth aspect of the present disclosure may include the seventeenth aspect where at least a portion of the 2-butene isomerizes to 1-butene in the metathesis reaction zone.

A nineteenth aspect of the present disclosure may include any of the first through eighteenth aspects where the metathesis reaction product comprises propylene and pentene.

A twentieth aspect of the present disclosure may include any of the first through nineteenth aspects where a volume ratio of the metathesis catalyst to the cracking catalyst is from 1:1 to 1:2.

A twenty-first aspect of the present disclosure may include any of the first through twentieth aspects where an acidity of the mesoporous silica-alumina catalyst support impregnated with metal oxide is from 0.001 mmol/g to 5 mmol/g.

A twenty-second aspect of the present disclosure may be directed to a multiple-stage catalyst system for producing propylene from butene, the multiple-stage catalyst system comprising a metathesis reaction zone and a cracking reaction zone downstream of the metathesis reaction zone, where the metathesis reaction zone comprises a mesoporous silica-alumina catalyst support impregnated with metal oxide having a mesoporous silica-alumina catalyst support that comprises from 5 weight percent to 50 weight percent alumina and the cracking reaction zone comprises a MFI structured silica-containing catalyst, where the MFI structured silica-containing catalyst cracks a metathesis product stream to form a cracking product stream comprising propylene.

A twenty-third aspect of the present disclosure may include the twenty-second aspect where the mesoporous silica-alumina catalyst support of the mesoporous silica-alumina catalyst support impregnated with metal oxide comprises from 10 weight percent to 40 weight percent alumina.

A twenty-fourth aspect of the present disclosure may include the twenty-second or twenty-third aspect where the mesoporous silica-alumina catalyst support impregnated with metal oxide includes a pore size distribution from 2.5 nm to 40 nm.

A twenty-fifth aspect of the present disclosure may include any of the twenty-second through twenty-fourth aspects where the mesoporous silica-alumina catalyst support impregnated with metal oxide includes a total pore volume of at least 0.600 cm$^3$/g.

A twenty-sixth aspect of the present disclosure may include any of the twenty-second through twenty-fifth aspects where the metal oxide of the mesoporous silica-alumina catalyst support impregnated with metal oxide comprises one or more oxides of molybdenum, rhenium, tungsten, or combinations of these oxides.

A twenty-seventh aspect of the present disclosure may include any of the twenty-second through twenty-fifth aspects where the metal oxide of the mesoporous silica-alumina catalyst support impregnated with metal oxide comprises tungsten oxide.

A twenty-eighth aspect of the present disclosure may include the twenty-seventh aspect where the mesoporous silica-alumina catalyst support impregnated with metal oxide comprises from 1 weight percent to 30 weight percent tungsten oxide.

A twenty-ninth aspect of the present disclosure may include the twenty-seventh aspect where the mesoporous silica-alumina catalyst support impregnated with metal oxide comprises from 5 weight percent to 20 weight percent tungsten oxide.

A thirtieth aspect of the present disclosure may include any of the twenty-second through twenty-ninth aspects where the MFI structured silica-containing catalyst comprises alumina.

A thirty-first aspect of the present disclosure may include any of the twenty-second through twenty-ninth aspects where the MFI structured silica-containing catalyst comprises less than 0.01 wt. % alumina.

A thirty-second aspect of the present disclosure may include any of the twenty-second through thirty-first aspects where the MFI structured silica-containing catalyst comprises a total acidity from 0.001 mmol/g to 0.1 mmol/g.

A thirty-third aspect of the present disclosure may include any of the twenty-second through thirty-second aspects where the metathesis reaction zone and the cracking reaction zone are disposed within a single reactor.

A thirty-fourth aspect of the present disclosure may include any of the twenty-second through thirty-third aspects further comprising a feed stream comprising butene.

A thirty-fifth aspect of the present disclosure may include the thirty-fourth aspect where the butene comprises 2-butene.

A thirty-sixth aspect of the present disclosure may include any of the thirty-fourth or thirty-fifth aspects where the feed stream is a raffinate-2 stream produced from a FCC reactor or an ethylene cracking reactor.

A thirty-seventh aspect of the present disclosure may include any of the thirty-fourth or thirty-fifth aspects where the feed stream comprises from 20 wt. % to 60 wt. % of cis- or trans-2-butene, or both, from 10 wt. % to 20 wt. % of 1-butene, and from 5 wt. % to 20 wt. % n-butane.

A thirty-eighth aspect of the present disclosure may include any of the twenty-second through thirty-seventh aspects where the volume ratio of the metathesis catalyst to the cracking catalyst is from 1:1 to 1:2.

A thirty-ninth aspect of the present disclosure may include any of the twenty-second through thirty-eighth aspects where an acidity of the mesoporous silica-alumina catalyst support impregnated with metal oxide is from 0.001 mmol/g to 5 mmol/g.

It is noted that one or more of the following claims utilize the term "where" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising." For the purposes of defining the present technology, the transitional phrase "consisting of" may be introduced in the claims as a closed preamble term limiting the scope of the claims to the recited components or steps and any naturally occurring impurities. For the purposes of defining the present technology, the transitional phrase "consisting essentially of" may be introduced in the claims to limit the scope of one or more claims to the recited elements, components, materials, or method steps as well as any non-recited elements, components, materials, or method steps that do not materially affect the novel characteristics of the claimed subject matter. The transitional phrases "consisting of" and "consisting essentially of" may be interpreted to be subsets of the open-ended transitional phrases, such as "comprising" and "including," such that any use of an open ended phrase to introduce a recitation of a series of elements, components, materials, or steps should be interpreted to also disclose recitation of the series of elements, components, materials, or steps using the closed terms "consisting of" and "consisting essentially of." For example, the recitation of a composition "comprising" components A, B and C should be interpreted as also disclosing a composition "consisting of" components A, B, and C as well as a composition "consisting essentially of" components A, B, and C. Any quantitative value expressed in the present application may be considered to include open-ended embodiments consistent with the transitional phrases "comprising" or "including" as well as closed or partially closed embodiments consistent with the transitional phrases "consisting of" and "consisting essentially of."

It should be understood that any two quantitative values assigned to a property may constitute a range of that property, and all combinations of ranges formed from all stated quantitative values of a given property are contemplated in this disclosure. It should be appreciated that compositional ranges of a chemical constituent in a stream or in a reactor should be appreciated as containing, in some embodiments, a mixture of isomers of that constituent. For example, a compositional range specifying butene may include a mixture of various isomers of butene. It should be appreciated that the examples supply compositional ranges for various streams, and that the total amount of isomers of a particular chemical composition can constitute a range.

Having described the subject matter of the present disclosure in detail and by reference to specific embodiments, it is noted that the various details described in this disclosure should not be taken to imply that these details relate to elements that are essential components of the various embodiments described in this disclosure, even in cases where a particular element is illustrated in each of the drawings that accompany the present description. Rather, the claims appended hereto should be taken as the sole representation of the breadth of the present disclosure and the corresponding scope of the various embodiments described in this disclosure. Further, it will be apparent that modifications and variations are possible without departing from the scope of the appended claims.

What is claimed is:

1. A multiple-stage catalyst system for producing propylene from butene, the multiple-stage catalyst system comprising a feed stream, a metathesis reaction zone and a cracking reaction zone directly downstream of the metathesis reaction zone, where:
   the metathesis reaction zone comprises a metathesis catalyst comprising a mesoporous silica-alumina catalyst support impregnated with at least one metal oxide, the mesoporous silica-alumina catalyst support comprising from 5 weight percent to 50 weight percent alumina;
   the cracking reaction zone comprises a cracking catalyst comprising an MFI structured silica-containing catalyst, where the MFI structured silica-containing catalyst directly cracks a metathesis product stream to form a cracking product stream comprising propylene; and
   the feed stream to the multiple-stage catalyst system comprises from 20 wt. % to 60 wt. % of cis- or trans-2-butene, or both, from 10 wt. % to 20 wt. % of 1-butene, and from 5 wt. % to 20 wt. % n-butene.

2. The multiple-stage catalyst system of claim 1 where the mesoporous silica-alumina catalyst support impregnated with at least one metal oxide comprises from 1 weight percent to 30 weight percent tungsten oxide.

3. The multiple-stage catalyst system of claim 1 where the metathesis reaction zone and the cracking reaction zone are disposed within a single reactor.

4. The multiple-stage catalyst system of claim 1 where the volume ratio of the metathesis catalyst to the cracking catalyst is from 1:1 to 1:2.

5. The multiple-stage catalyst system of claim 1 where the mesoporous silica-alumina catalyst support comprises from 10 weight percent to 40 weight percent alumina.

6. The multiple-stage catalyst system of claim 1 where the metathesis catalyst includes a pore size distribution from 2.5 nm to 40 nm.

7. The multiple-stage catalyst system of claim 1 where the at least one metal oxide comprises one or more oxides of molybdenum, rhenium, tungsten, or combinations of these oxides.

8. The multiple-stage catalyst system of claim 1 where the at least one metal oxide of the mesoporous silica-alumina catalyst support impregnated with at least one metal oxide comprises tungsten oxide.

9. The multiple-stage catalyst system of claim 1 where the at least one metal oxide comprises tungsten oxide and the metathesis catalyst comprises from 5 weight percent to 20 weight percent tungsten oxide.

10. The multiple-stage catalyst system of claim 1 where the MFI structured silica-containing catalyst comprises alumina.

11. The multiple-stage catalyst system of claim 1 where the MFI structured silica-containing catalyst comprises less than 0.01 wt. % alumina.

12. The multiple-stage catalyst system of claim 1 where the MFI structured silica-containing catalyst comprises a total acidity from 0.001 mmol/g to 0.1 mmol/g.

13. The multiple-stage catalyst system of claim 1 where an acidity of the metathesis catalyst is from 0.001 mmol/g to 5 mmol/g.

14. The multiple-stage catalyst system of claim 1 in which the metathesis catalyst is disposed in a first reactor, the cracking catalyst is disposed in a second reactor downstream of the first reactor, and a direct conduit extends between the first reactor and second reactor so that the cracking catalyst directly cracks the metathesis product stream.

15. The multiple-stage catalyst system of claim 1 where the metathesis reaction zone is positioned directly against the cracking reaction zone.

16. A multiple-stage catalyst system for producing propylene from butene, the multiple-stage catalyst system comprising a metathesis reaction zone and a cracking reaction zone directly downstream of the metathesis reaction zone, where:
   the metathesis reaction zone comprises a metathesis catalyst comprising a mesoporous silica-alumina catalyst support impregnated with at least one metal oxide, the mesoporous silica-alumina catalyst support comprising from 5 weight percent to 50 weight percent alumina;
   the metathesis catalyst includes a relative pore volume per weight of the metathesis catalyst of at least 0.600 cm$^3$/g; and
   the cracking reaction zone comprises a cracking catalyst comprising an MFI structured silica-containing catalyst, where the MFI structured silica-containing catalyst directly cracks a metathesis product stream to form a cracking product stream comprising propylene.

17. The multiple-stage catalyst system of claim 16 in which the metathesis catalyst is disposed in a first reactor, the cracking catalyst is disposed in a second reactor downstream of the first reactor, and a direct conduit extends between the first reactor and second reactor so that the cracking catalyst directly cracks the metathesis product stream.

18. The multiple-stage catalyst system of claim 16 where the metathesis reaction zone is positioned directly against the cracking reaction zone.

19. The multiple-stage catalyst system of claim 16 further comprising a feed stream comprising butene.

20. The multiple-stage catalyst system of claim 19 where the butene comprises 2-butene.

* * * * *